(12) United States Patent
Ogawa

(10) Patent No.: US 11,337,595 B2
(45) Date of Patent: May 24, 2022

(54) ENDOSCOPE APPARATUS FOR DETERMINING SITUATION OF OCCURRENCE OF ROLLING DISTORTION

(71) Applicant: OLYMPUS CORPORATION, Tokyo (JP)

(72) Inventor: Kiyotomi Ogawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 532 days.

(21) Appl. No.: 16/387,831

(22) Filed: Apr. 18, 2019

(65) Prior Publication Data

US 2019/0239732 A1 Aug. 8, 2019

Related U.S. Application Data

(63) Continuation of application No. PCT/JP2017/037823, filed on Oct. 19, 2017.

(30) Foreign Application Priority Data

Oct. 24, 2016 (JP) .............................. JP2016-207698

(51) Int. Cl.
*A61B 1/045* (2006.01)
*A61B 1/06* (2006.01)
(Continued)

(52) U.S. Cl.
CPC .......... *A61B 1/045* (2013.01); *A61B 1/00163* (2013.01); *A61B 1/0676* (2013.01);
(Continued)

(58) Field of Classification Search
None
See application file for complete search history.

(56) References Cited

U.S. PATENT DOCUMENTS

2011/0267514 A1* 11/2011 D'Angelo ............ H04N 5/2329
348/296
2014/0225998 A1* 8/2014 Dai ...................... H04N 5/3532
348/65
(Continued)

FOREIGN PATENT DOCUMENTS

JP 2008-029621 A 2/2008
JP 2011-206336 A 10/2011
(Continued)

OTHER PUBLICATIONS

International Search Report dated Nov. 28, 2017 issued in PCT/JP2017/037823.

*Primary Examiner* — John P Leubecker
(74) *Attorney, Agent, or Firm* — Scully, Scott, Murphy & Presser, P.C.

(57) ABSTRACT

When a first mode is set in an endoscope apparatus, a light source control unit causes a light source to be turned on during a period including all or a part of a period during which available storage periods of pixels in all simultaneous exposure lines. An imaging device generates a first image. When a second mode is set, the light source control unit causes the light source to be turned on during a period including all of the available storage period of the pixels in each of a plurality of rows. The imaging device generates a second image. The rolling distortion determination unit determines a situation of occurrence of rolling distortion using the first image and the second image.

19 Claims, 23 Drawing Sheets

(51) Int. Cl.
*H04N 5/225* (2006.01)
*A61B 1/00* (2006.01)
*G02B 23/24* (2006.01)
*H04N 5/341* (2011.01)
*G02B 23/26* (2006.01)

(52) U.S. Cl.
CPC ......... *G02B 23/24* (2013.01); *G02B 23/2461* (2013.01); *G02B 23/26* (2013.01); *H04N 5/341* (2013.01); *A61B 1/00006* (2013.01); *H04N 2005/2255* (2013.01)

(56) References Cited

U.S. PATENT DOCUMENTS

| | | | |
|---|---|---|---|
| 2015/0296159 A1* | 10/2015 | Mansoorian | H04N 5/2329 348/308 |
| 2017/0027416 A1 | 2/2017 | Hayashi | |
| 2018/0234646 A1* | 8/2018 | Kobayashi | H04N 5/3696 |
| 2019/0149750 A1* | 5/2019 | Thebault | H04N 5/2353 348/302 |

FOREIGN PATENT DOCUMENTS

| | | |
|---|---|---|
| JP | 2011-244951 A | 12/2011 |
| JP | 2014-004103 A | 1/2014 |
| JP | 2015-139646 A | 8/2015 |
| JP | 2015-164284 A | 9/2015 |
| WO | WO 2015/115067 A1 | 8/2015 |

* cited by examiner

ENDOSCOPE APPARATUS FOR DETERMINING SITUATION OF OCCURRENCE OF ROLLING DISTORTION

The present application claims priority to Japanese Patent Application No. 2016-207698, filed on Oct. 24, 2016, and is a continuation application based on PCT Patent Application No. PCT/JP2017/037823, filed on Oct. 19, 2017, and the contents of both the Japanese patent application and the PCT patent application are incorporated herein by reference.

BACKGROUND OF THE INVENTION

Field of the Invention

The present invention relates to an endoscope apparatus.

Description of Related Art

In an imaging apparatus using a complementary metal oxide semiconductor (CMOS) imager as an imaging device, a circuit configuration is simplified and power consumption is reduced as compared with a case in which a charge coupled device (CCD) is used. Sequential line exposure reading (a rolling shutter operation) is generally adopted as a reading method of the CMOS imager. In this reading method, rolling shutter distortion (rolling distortion) due to a time difference in exposure timing between lines of the CMOS imager is known to occur in an image captured on condition that a camera or a subject is moving.

In an endoscope apparatus, a situation in which it is difficult to fix a distal end of an endoscope or a situation of inspection in which a subject has motion are assumed. Thus, when a CMOS imager is used in an imaging device, it is desirable that rolling distortion not occur to capture a high-quality image. In particular, in endoscopic inspection in industrial fields, countermeasures against rolling distortion are important to reduce measurement errors because the number of applications requiring dimensional measurement of defects of a subject has recently increased.

As disclosed in Japanese Unexamined Patent Application, First Publication Nos. 2008-029621 and 2011-206336, global exposure is performed as a countermeasure against rolling distortion. In control of the global exposure, an available charge storage period is started by simultaneously resetting charges stored in all pixels of the CMOS imager during a period in which illumination is turned off. Also, the illumination is turned on during the available charge storage period of all the pixels, so that the exposure is started simultaneously for all the pixels. Thereby, imaging is performed in all the pixels. After a process in which all the pixels are exposed at the same time by turning off the illumination is completed, charges of the pixels are sequentially read. According to such control, the timing of exposure for imaging coincides in all pixels.

SUMMARY OF THE INVENTION

According to a first aspect of the present invention, an endoscope apparatus includes a light source, a light source control unit, an optical system, an imaging device, an imaging device control unit, a rolling distortion determination unit, and a mode setting unit. The light source generates illumination light for illuminating a subject. The light source control unit controls turning on and off of the light source. The optical system forms an optical image of the subject illuminated with the illumination light. The imaging device includes a plurality of pixels disposed in a matrix and generates pixel signals of the pixels based on the optical image in each of a plurality of frames and generates an image of the subject using the pixel signals. The imaging device control unit controls the imaging device. The rolling distortion determination unit determines a situation of occurrence of rolling distortion in the image. The mode setting unit performs switching between settings of a first mode and a second mode for the light source control unit and the imaging device control unit. When the first mode is set, the imaging device control unit causes the imaging device to perform a first scan for reading the pixel signals from the pixels in simultaneous exposure lines by consecutively scanning all the simultaneous exposure lines. The simultaneous exposure lines are some of a plurality of rows in an array of the plurality of pixels. When the first mode is set, the light source control unit causes the light source to be turned on during a first period and causes the light source to be turned off during a period including all of a second period. The first period is a period including all or a part of a period during which available storage periods of the pixels in all the simultaneous exposure lines overlap. The second period is a period during which a scan is performed for reading the pixel signals generated by the pixels in all the simultaneous exposure lines from the pixels during the first period. The imaging device generates a first image using the pixel signals generated by the pixels in all the simultaneous exposure lines during the period in which the available storage periods of the pixels in all the simultaneous exposure lines overlap. When the second mode is set, the imaging device control unit causes the imaging device to perform a second scan for reading the pixel signals from the pixels in the plurality of rows by consecutively scanning the plurality of rows. When the second mode is set, the light source control unit causes the light source to be turned on during a period including all of the available storage period of the pixels in each of the plurality of rows before the second scan is performed. The imaging device generates a second image using the pixel signals read by the second scan. The rolling distortion determination unit determines the situation of the occurrence of the rolling distortion using the first image and the second image.

According to a second aspect of the present invention, in the first aspect, the rolling distortion determination unit may determine the situation of the occurrence of the rolling distortion using data of the simultaneous exposure lines of the first image and data of rows corresponding to the simultaneous exposure lines of the first image in the second image.

According to a third aspect of the present invention, in the first aspect, the imaging device control unit may cause the imaging device to read the pixel signals of a second frame from the pixels in rows including all the simultaneous exposure lines after the pixel signals of a first frame are read from the pixels in all the simultaneous exposure lines by the first scan. The imaging device may generate the first image using the pixel signals of the second frame. After a scan of all the simultaneous exposure lines by the first scan is completed, the light source control unit may cause the light source to be turned on during a period including all or a part of a period during which the available storage periods of the pixels in all the simultaneous exposure lines overlap and cause the light source to be turned off during a period including all of a period during which the first scan is performed. The light source control unit may cause the light source to be turned off during a period in which the pixel signals of the second frame are read from the pixels in the simultaneous exposure lines.

According to a fourth aspect of the present invention, in the first aspect, when the first mode is set, the imaging device control unit may cause the imaging device to simultaneously reset the pixels in all the simultaneous exposure lines. After the pixels in all the simultaneous exposure lines are simultaneously reset, the imaging device control unit may cause the imaging device to perform the first scan. The imaging device may generate the first image using the pixel signals read by the first scan. After the pixels in all the simultaneous exposure lines are simultaneously reset, the light source control unit may cause the light source to be turned on during the first period and cause the light source to be turned off during a period including all of a period during which the first scan is performed.

According to a fifth aspect of the present invention, in the first aspect, the endoscope apparatus may further include a blur determination unit configured to determine a situation of occurrence of a blur in the first image. When an instruction of any one of freezing, image recording, and measurement is accepted, the mode setting unit may set the first mode in the light source control unit and the imaging device control unit. When the blur determination unit determines that a blur in the first image is less than or equal to a predetermined amount, the mode setting unit may set the second mode in the light source control unit and the imaging device control unit.

According to a sixth aspect of the present invention, in the first aspect, the endoscope apparatus may further include a blur determination unit configured to determine a situation of occurrence of a blur in the first image and the second image. When an instruction of any one of freezing, image recording, and measurement is accepted, the blur determination unit may determine a situation of occurrence of a blur in the second image. When the blur determination unit determines that a blur in the second image is less than or equal to a predetermined amount, the mode setting unit may set the first mode in the light source control unit and the imaging device control unit. When the blur determination unit determines that a blur in the first image is less than or equal to a predetermined amount, the mode setting unit may set the second mode in the light source control unit and the imaging device control unit.

According to a seventh aspect of the present invention, in the first aspect, the endoscope apparatus may further include a processing unit configured to perform a process using the second image for which the rolling distortion unit determines that the rolling distortion is less than or equal to a predetermined amount.

According to an eighth aspect of the present invention, in the seventh aspect, the processing unit may be a recording unit configured to record the second image for which the rolling distortion determination unit determines that the rolling distortion is less than or equal to the predetermined amount in a memory after an image recording instruction is accepted.

According to a ninth aspect of the present invention, in the seventh aspect, the processing unit may be a measurement unit configured to perform measurement of the subject using the second image for which the rolling distortion determination unit determines that the rolling distortion is less than or equal to the predetermined amount after a measurement instruction is accepted.

According to a tenth aspect of the present invention, in the first aspect, the endoscope apparatus may further include a temperature sensor configured to measure a temperature of the imaging device. The mode setting unit may perform switching between the first mode, the second mode, and a third mode for the light source control unit and the imaging device control unit. When the temperature is greater than a predetermined value, the mode setting unit may sequentially set the first mode and the second mode in the light source control unit and the imaging device control unit. When the temperature is less than or equal to the predetermined value, the mode setting unit may sequentially set the third mode in the light source control unit and the imaging device control unit. When the third mode is set, the imaging device control unit may cause the imaging device to perform the second scan during a period shorter than a frame cycle. The imaging device may generate a third image using the pixel signals read by the second scan in the third mode. The light source control unit may cause the light source to be turned on during a period including all or a part of a period during which the available storage periods of the pixels in each of the plurality of rows overlap before the second scan is performed in the third mode. The light source control unit may cause the light source to be turned off during a period in which the second scan is performed in the third mode.

According to an eleventh aspect of the present invention, in the first aspect, the endoscope apparatus may further include a display unit configured to display only the second image between the first image and the second image.

According to a twelfth aspect of the present invention, in the eleventh aspect, the display unit may display a warning when the rolling distortion determination unit determines that the rolling distortion greater than a predetermined amount has occurred.

According to a thirteenth aspect of the present invention, in the first aspect, the endoscope apparatus may further include a display unit configured to display the situation of the occurrence of the rolling distortion determined by the rolling distortion determination unit.

According to a fourteenth aspect of the present invention, in the eleventh aspect, after a freeze instruction is accepted, the display unit may perform a freeze display process on the second image for which the rolling distortion determination unit determines that the rolling distortion is less than or equal to a predetermined amount.

According to a fifteenth aspect of the present invention, in the twelfth aspect, the endoscope apparatus may further include a processing unit configured to perform a process using the second image for which the rolling distortion determination unit determines that the rolling distortion is less than or equal to the predetermined amount when a processing instruction is accepted after the display unit displays the warning.

According to a sixteenth aspect of the present invention, in the tenth aspect, the endoscope apparatus may further include a display unit configured to display only the second image among the first image, the second image, and the third image.

According to a seventeenth aspect of the present invention, in the tenth aspect, the endoscope apparatus may further include a display unit configured to display only the second image and the third image among the first image, the second image, and the third image.

DETAILED DESCRIPTION OF THE INVENTION

Hereinafter, embodiments of the present invention will be described with reference to the drawings.

First Embodiment

Figure 1:
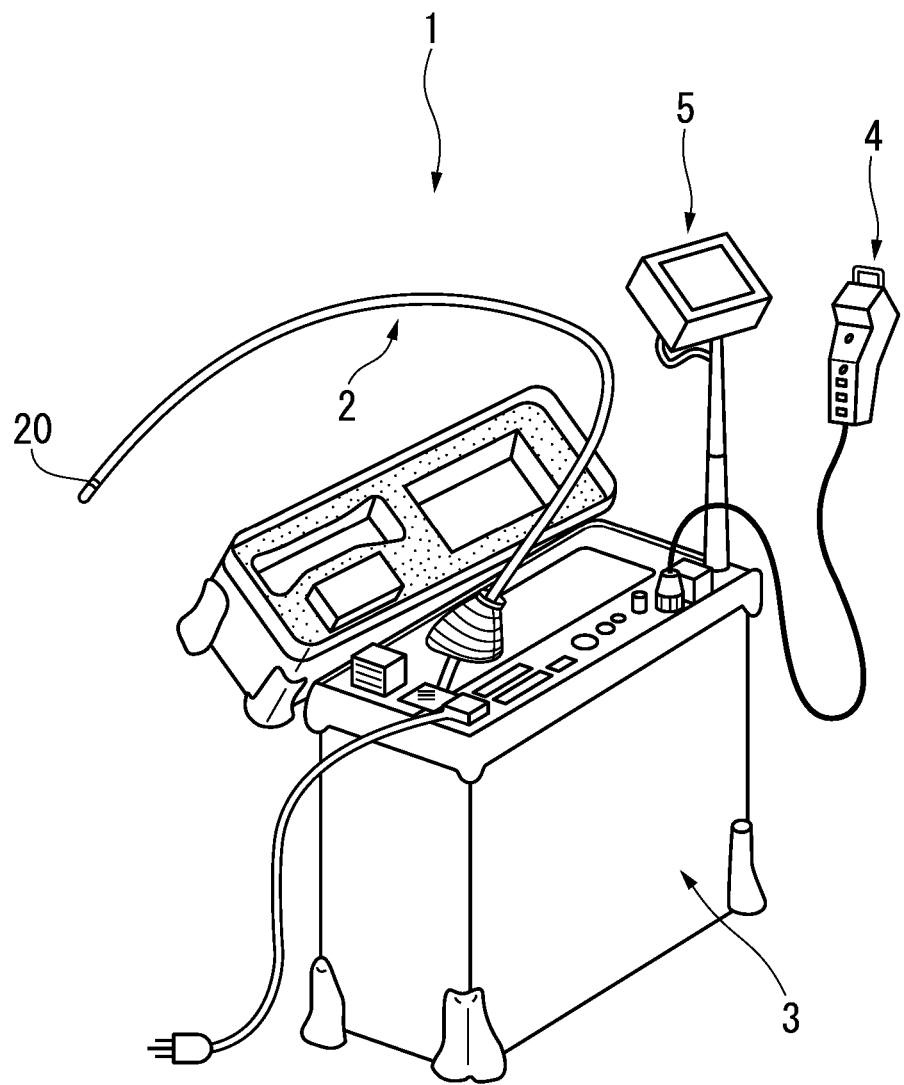
FIG. 1 is a perspective view showing an overall configuration of an endoscope apparatus according to a first embodiment of the present invention.
Figure 2:
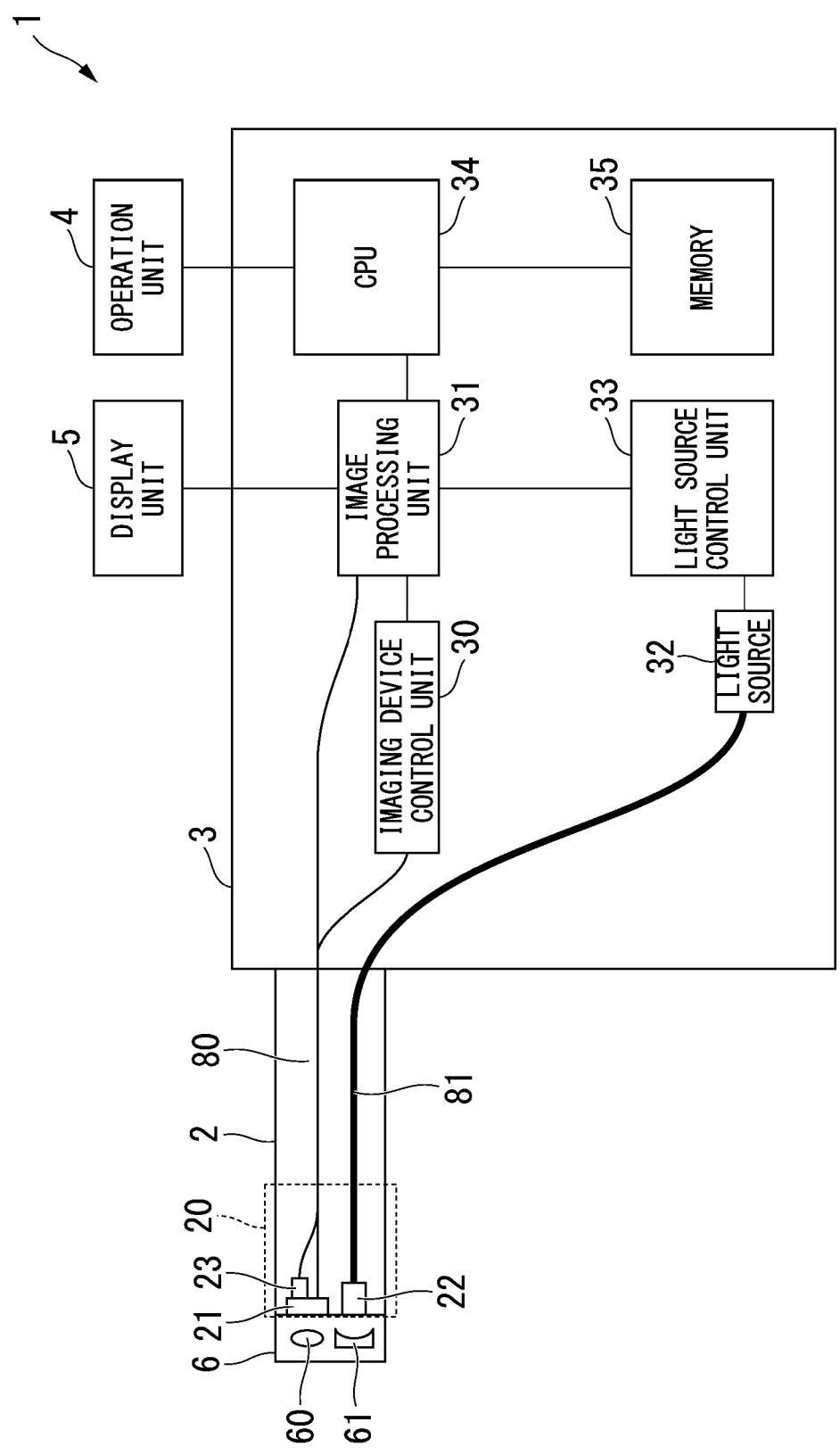
FIG. 2 is a block diagram showing a detailed configuration of the endoscope apparatus according to the first embodiment of the present invention.

FIG. 1 shows an overall configuration of an endoscope apparatus 1 according to a first embodiment of the present invention. FIG. 2 shows an internal configuration of the endoscope apparatus 1. As shown in FIG. 1, the endoscope apparatus 1 includes an insertion unit 2, a control unit 3, an operation unit 4, and a display unit 5.

The insertion unit 2 is inserted into an object to be observed. An optical adapter having an optical system for taking light from a subject into the distal end 20 can be attached to a distal end 20 (a distal end portion) of the insertion unit 2. For example, by attaching a stereo optical adapter to the distal end 20, it is possible to acquire two subject images corresponding to a plurality of different viewpoints. Using stereo images of the two subject images, the endoscope apparatus 1 can measure dimensions of the subject according to a triangulation principle. The control unit 3 has a configuration for controlling the endoscope apparatus 1. The operation unit 4 accepts an operation performed by the user. The display unit 5 displays images captured by the endoscope apparatus 1, a processing menu, and the like.

FIG. 2 shows a detailed configuration of the endoscope apparatus 1. As shown in FIG. 2, an optical adapter 6 is attached to the distal end 20 of the insertion unit 2. The optical adapter 6 of the first embodiment is a stereo optical adapter for forming a plurality of images from a plurality of viewpoints. The optical adapter 6 has an observation optical system 60 and an illumination optical system 61. The imaging device 21 is disposed at the distal end 20 of the insertion unit 2. The control unit 3 includes an imaging device control unit 30, an image processing unit 31, a light source 32, a light source control unit 33, a CPU 34, and a memory 35.

The light source 32 converts power supplied from the light source control unit 33 into blue excitation light, thereby generating illumination light for illuminating the subject. For example, the light source 32 is a semiconductor light-emitting device such as a light-emitting diode (LED) and a laser diode (LD). The semiconductor light-emitting element can perform switching between ON and OFF of light at high speed. Thus, when the semiconductor light-emitting element is instantaneously turned on, there is an effect in which deterioration of image quality due to camera shake and subject shake, i.e., occurrence of a motion blur, is minimized. Because the semiconductor light-emitting element has higher light emission efficiency than other light sources such as halogen lamps, the power consumption is less than that of other light sources of the same brightness and the endoscope apparatus 1 can also be miniaturized.

The light source control unit 33 supplies power to the light source 32 and controls timings of turning-on and turning-off of the light source 32 and an intensity of emitted light on the basis of light source control parameters output from the image processing unit 31. A control mode of the light source 32 includes a consecutive turn-on mode and a pulse turn-on mode. In the consecutive turn-on mode, an intensity of light is controlled by a magnitude of a direct current supplied to the light source 32. In the pulse turn-on mode, an intensity of light is controlled by a width and a height of a current pulse supplied to the light source 32.

The excitation light emitted from the light source 32 is transmitted to the distal end 20 of the insertion unit 2 via a light guide 81 disposed within the insertion unit 2 and the control unit 3. The light guide 81 is an optical fiber bundle in which strands of the optical fiber are bundled. The excitation light is converted into white light by a fluorescent substance 22 disposed at the distal end 20. An illumination optical system 61 irradiates the subject with white light. The insertion unit 2 is inserted into the object and irradiates the subject with the light generated by the light source 32 via the optical adapter 6 (the illumination optical system 61) attached to the distal end 20.

The observation optical system 60 receives light reflected on a surface of the subject illuminated with white light. In other words, the observation optical system 60 forms an optical image of the subject illuminated with the illumination light. The light received by the observation optical system 60 is incident on the imaging device 21. The imaging device 21 captures an image of the subject inside an object into which the insertion unit 2 is inserted from a plurality of viewpoints and generates image data of the optical image of the subject. For example, a CMOS imager using a line exposure method is used for the imaging device 21. By adopting the CMOS imager, it is possible to make the endoscope apparatus 1 simple and reduce the power consumption of the endoscope apparatus 1.

A signal line 80 disposed within the insertion unit 2 and the control unit 3 is a composite coaxial line constituted by bundling a plurality of coaxial cables. A distal end side of the signal line 80 is connected to the imaging device 21 and a part of the coaxial cable on a base end side of the signal line 80 is connected to the imaging device control unit 30. The imaging device control unit 30 supplies power for driving to the imaging device 21 via the signal line 80. Also, the imaging device control unit 30 controls the imaging device 21 by outputting imaging parameters received from the image processing unit 31 to the imaging device 21.

The remaining coaxial cable on the base end side of the signal line 80 is connected to the image processing unit 31. The image data generated by the imaging device 21 is transmitted to the image processing unit 31. The image processing unit 31 performs various types of image processing on the image data output from the imaging device 21. For example, the image processing performed by the image processing unit 31 is at least one of demosaicing, digital gain adjustment, noise reduction, white balance adjustment, contour correction, and gamma correction. Also, the image processing unit 31 generates a video signal for display by synthesizing image data on which image processing has been performed with graphic data generated by the CPU 34. The image processing unit 31 outputs the generated video signal for display to the display unit 5. The display unit 5 displays an image of the subject on the basis of the video signal output from the image processing unit 31.

Further, the image processing unit 31 generates imaging device control parameters and light source control parameters on the basis of the input image data to perform imaging with appropriate brightness. The imaging device control parameters are parameters such as an electronic shutter speed, an analog gain, and a driving mode. The light source control parameters are parameters such as an ON/OFF timing and a turn-on intensity. The image processing unit 31 outputs the imaging device control parameters to the imaging device control unit 30. The imaging device control unit 30 controls the imaging device 21 on the basis of the imaging device control parameters. The image processing unit 31 outputs the light source control parameters to the light source control unit 33. The light source control unit 33 controls the light source 32 on the basis of the light source control parameters.

At the distal end 20 of the insertion unit 2, a temperature sensor 23 is disposed in the vicinity of the imaging device 21. The temperature sensor 23 may be in contact with the imaging device 21. The temperature sensor 23 measures a temperature of the imaging device 21. The temperature sensor 23 outputs temperature data indicating the measured temperature to the signal line 80. The temperature data output from the temperature sensor 23 is transmitted to the CPU 34 via the image processing unit 31.

The CPU 34 controls each unit within the endoscope apparatus 1. Also, the CPU 34 monitors a state of the operation unit 4. Thereby, the CPU 34 detects operations related to measurement and the like. Also, the CPU 34 detects the temperature of the imaging device 21 on the basis of the temperature data output from the temperature sensor 23.

The memory 35 stores the image data processed by the image processing unit 31. The memory 35 may be detachable from the endoscope apparatus 1.

Figure 3:
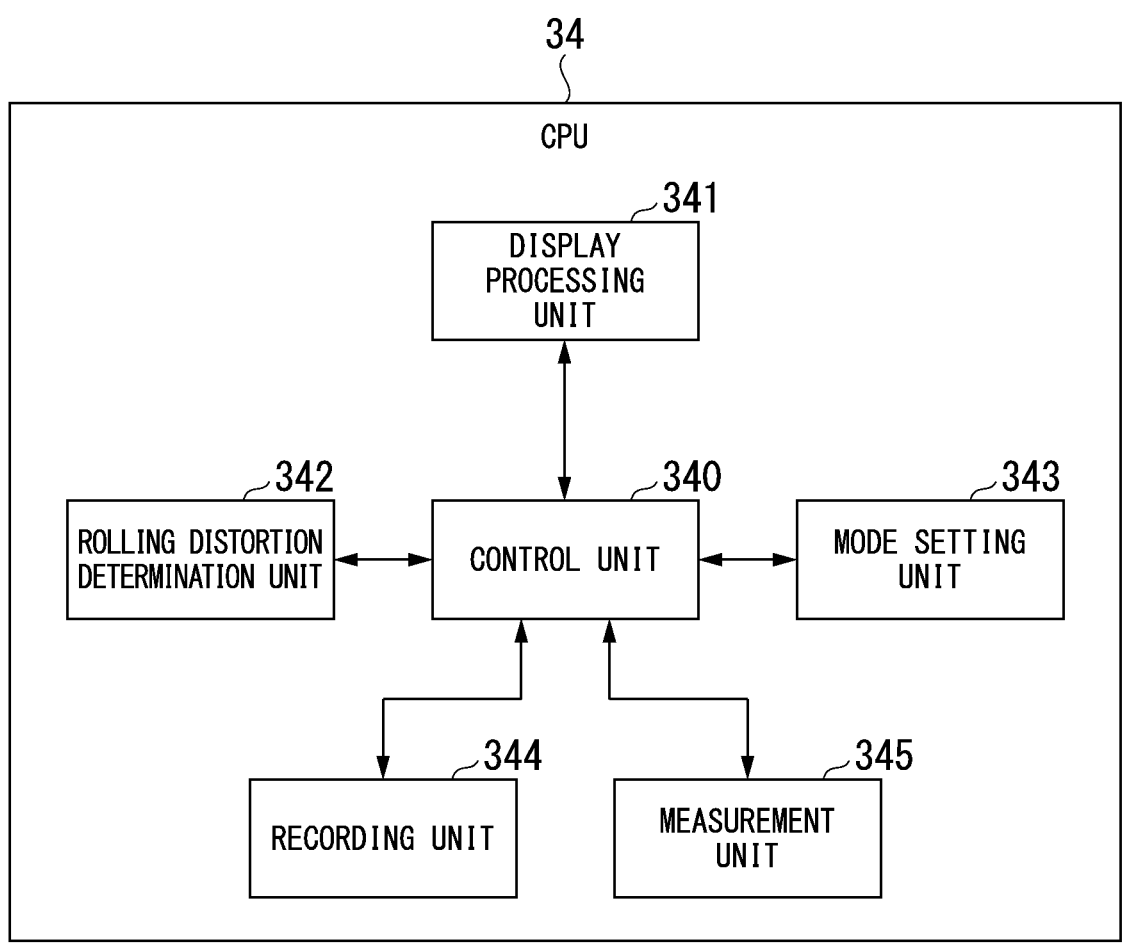
FIG. 3 is a block diagram showing a functional configuration of a CPU according to the first embodiment of the present invention.

FIG. 3 shows a functional configuration of the CPU 34. Functions of the CPU 34 are constituted by a control unit 340, a display processing unit 341, a rolling distortion determination unit 342, a mode setting unit 343, a recording unit 344, and a measurement unit 345. At least one of the blocks shown in FIG. 3 may include a circuit different from the CPU 34.

The control unit 340 controls a process to be performed by each unit. When the user operates the operation unit 4, the control unit 340 accepts an operation performed by the user. The display processing unit 341 generates graphic data for displaying menus and the like. The graphic data generated by the display processing unit 341 is output to the image processing unit 31. Also, the display processing unit 341 controls a state of an image displayed on the display unit 5 by controlling the image processing unit 31. The rolling distortion determination unit 342 determines a situation of occurrence of rolling distortion in the image of the subject. The mode setting unit 343 performs switching between settings of a semi-global (SG) exposure mode (a first mode) and a line exposure mode (a second mode) for the light source control unit 33 and the imaging device control unit 30. The SG exposure mode and the line exposure mode will be described below. The mode setting unit 343 outputs mode information to the image processing unit 31. The mode information indicates the mode to be set. The image processing unit 31 generates an imaging device control parameter and a light source control parameter corresponding to a mode indicated by the mode information. The recording unit 344 records the image of the subject, i.e., image data, in the memory 35. The measurement unit 345 measures the subject using the image of the subject, i.e., the image data.

Figure 4:
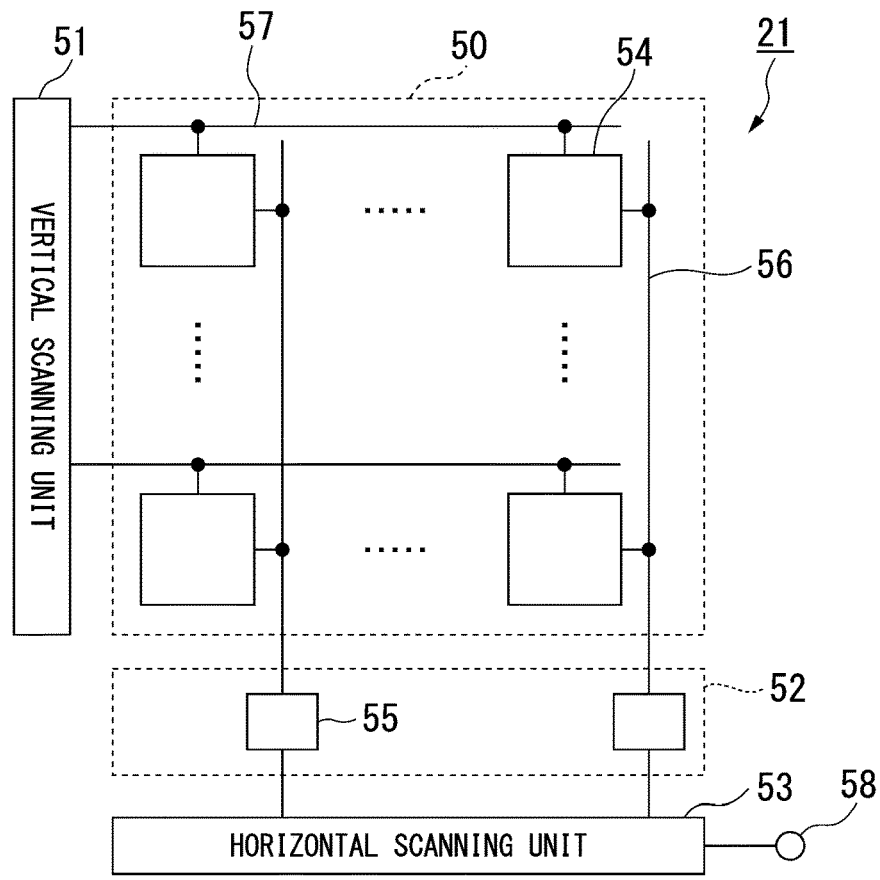
FIG. 4 is a block diagram showing a configuration of an imaging device in the first embodiment of the present invention.

FIG. 4 shows a configuration of the imaging device 21. As shown in FIG. 4, the imaging device 21 includes a pixel unit 50, a vertical scanning unit 51, a signal processing unit 52, and a horizontal scanning unit 53.

The pixel unit 50 includes a plurality of pixels 54 disposed in a matrix. The plurality of pixels 54 are disposed in an imaging region of the imaging device 21. Each of the number of rows and the number of columns in an array of the plurality of pixels 54 is two or more. The number of rows and the number of columns may not be the same. Each of the plurality of pixels 54 generates a pixel signal in accordance with an intensity of light incident on the pixel 54. Each of the plurality of pixels 54 is connected to a vertical signal line 56. A plurality of vertical signal lines 56 are disposed. Each of the plurality of vertical signal lines 56 is disposed for one column in the array of the plurality of pixels 54. Each of the plurality of pixels 54 outputs a generated pixel signal to the vertical signal line 56.

Each of the plurality of pixels 54 is connected to a control signal line 57. A plurality of control signal lines 57 are disposed. Each of the plurality of control signal lines 57 is disposed for one row in the array of the plurality of pixels 54. Each of the plurality of control signal lines 57 is connected to the vertical scanning unit 51. A control signal for controlling the operation of the plurality of pixels 54 is output from the vertical scanning unit 51 to the control signal line 57. A plurality of control signal lines 57 are disposed for pixels 54 of one row. One control signal line 57 is shown for the pixels 54 of one row in FIG. 4 and the other control signal lines 57 are omitted. Details of control signals will be described below.

The operation of the plurality of pixels 54 is controlled on the basis of the control signals output to the control signal line 57. The control signals corresponding to the pixels 54 of one row are supplied in common to all the pixels 54 in the row. Thus, the same operation timing is set for two or more pixels 54 disposed in the same row. In other words, two or more pixels 54 disposed in the same row operate simultaneously. Details of the configuration of the pixel 54 will be described below.

A control signal generated by the imaging device control unit 30 is transmitted to the imaging device 21. The vertical scanning unit 51 generates a control signal for controlling the operation of the plurality of pixels 54 on the basis of the control signal received by the imaging device 21. The vertical scanning unit 51 generates a control signal corresponding to each of the plurality of rows in an array of the plurality of pixels 54. The vertical scanning unit 51 outputs the generated control signal to the control signal line 57.

The signal processing unit 52 includes a plurality of signal processing circuits 55. The signal processing circuit 55 is disposed for each column in the array of the plurality of pixels 54. The signal processing circuit 55 is connected to the vertical signal line 56. The signal processing circuit 55 performs signal processing including amplification, noise removal, and the like on the pixel signal output from the pixel 54 to the vertical signal line 56.

The pixel signal processed by the signal processing circuit 55 is input to the horizontal scanning unit 53. The horizontal scanning unit 53 sequentially selects columns in the array of the plurality of pixels 54. The pixel signal corresponding to the column selected by the horizontal scanning unit 53 is output from an output terminal 58.

As described above, the imaging device 21 includes a plurality of pixels 54 disposed in a matrix. In each of a plurality of frames, the imaging device 21 generates a pixel signal of each pixel 54 on the basis of the optical image of the subject illuminated with the illumination light, and generates an image of the subject using the pixel signal.

Figure 5:
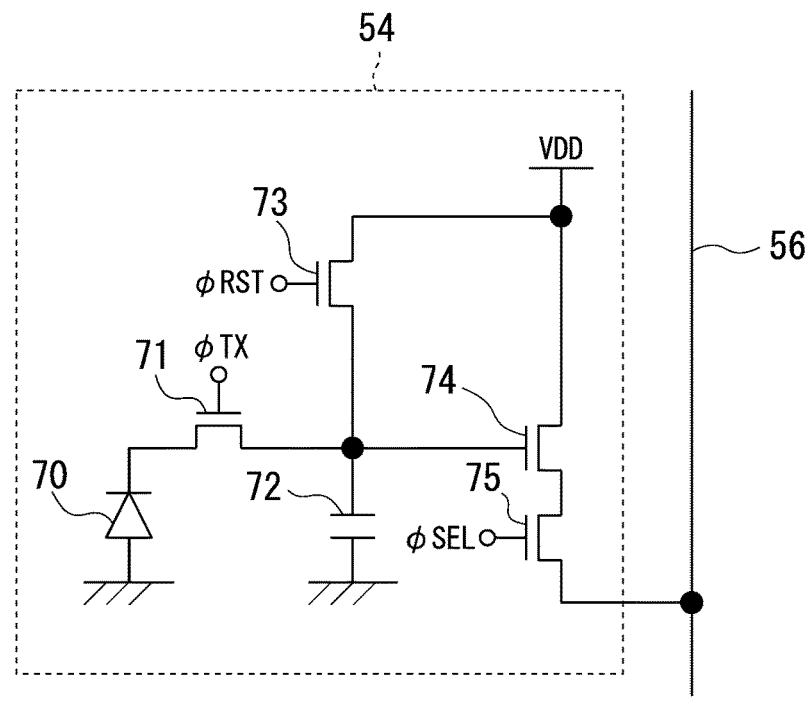
FIG. 5 is a circuit diagram showing a configuration of a pixel in the first embodiment of the present invention.

FIG. 5 shows a configuration of the pixel 54. As shown in FIG. 5, the pixel 54 includes a photoelectric conversion unit 70, a charge transfer unit 71, a charge storage unit 72, a resetting unit 73, an amplification unit 74, and an output unit 75. The photoelectric conversion unit 70 is a photodiode. The charge storage unit 72 is a capacitor. For example, the charge storage unit 72 is a gate capacitor of a transistor which constitutes the amplification unit 74. The charge transfer unit 71, the resetting unit 73, the amplification unit 74, and the output unit 75 are transistors.

The photoelectric conversion unit 70 generates charges in accordance with an intensity of light incident on the pixel 54. The charge transfer unit 71 transfers the charges generated by the photoelectric conversion unit 70 to the charge storage unit 72. The charge storage unit 72 stores the charges transferred from the photoelectric conversion unit 70. The resetting unit 73 resets the charges in the photoelectric conversion unit 70 and the charge storage unit 72 on the basis of a power-supply voltage VDD. By turning the charge transfer unit 71 and the resetting unit 73 on, the resetting unit 73 can reset the charges in the photoelectric conversion unit 70 and the charge storage unit 72. The amplification unit 74 amplifies a signal on the basis of the charges stored in the charge storage unit 72. The output unit 75 outputs the signal amplified by the amplification unit 74 as a pixel signal to the vertical signal line 56.

An operation of the charge transfer unit 71 is controlled by a control signal φTX. An operation of the resetting unit 73 is controlled by a control signal φRST. An operation of the output unit 75 is controlled by a control signal φSEL. The control signal φTX, the control signal φRST, and the control signal φSEL are supplied from the vertical scanning unit 51 via the control signal line 57.

The operation of the pixel 54 includes resetting, a charge transfer, and reading. The resetting corresponds to the operation of the resetting unit 73. The charge transfer corresponds to the operation of the charge transfer unit 71. The reading corresponds to the operation of the output unit 75.

A method of controlling the imaging device 21 and the light source 32 in the first embodiment will be described with reference to FIGS. 6 to 8. In the first embodiment, the endoscope apparatus 1 can perform switching between operations based on a plurality of modes.

Figure 6:
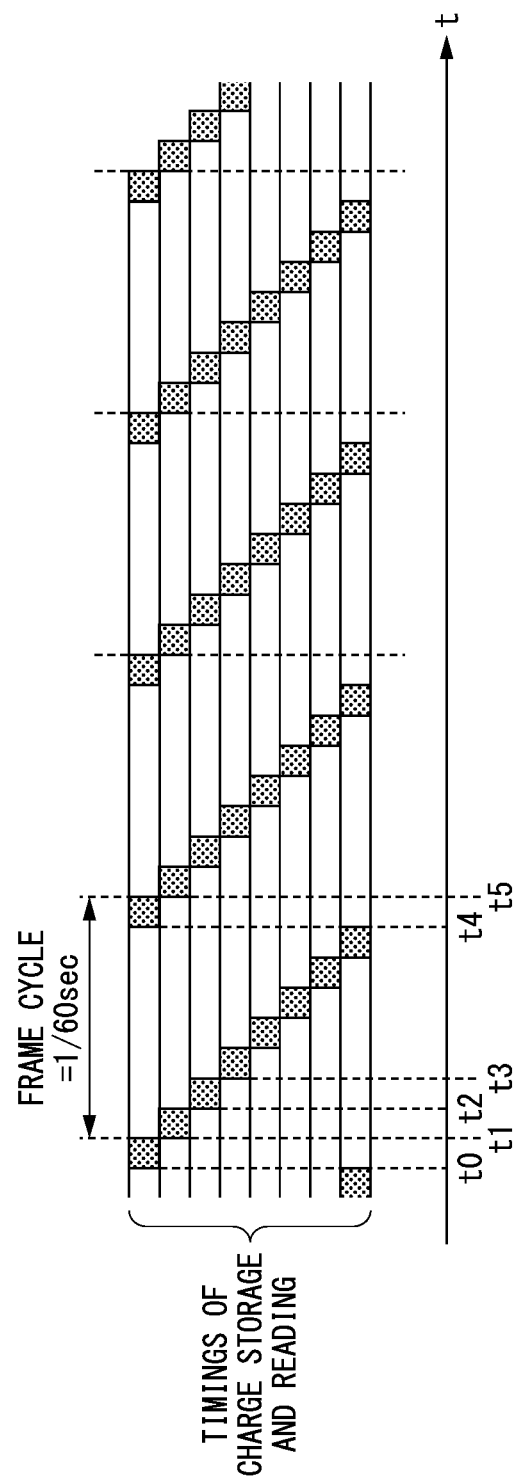
FIG. 6 is a timing chart showing an operation of an imaging device in the first embodiment of the present invention.

FIG. 6 shows an operation of the imaging device 21 in the line exposure mode. In FIG. 6, a horizontal direction indicates time and a vertical direction indicates a row position of the pixel 54 of the imaging device 21. In FIG. 6, operations in the pixels 54 of eight rows are shown. A top row is a first row and a bottom row is an eighth row.

In FIG. 6, a cycle of imaging, i.e., a frame cycle, is 1/60 sec and a time required for reading pixel signals of all the pixels 54 in the operation of each frame is 1/60 sec. In FIG. 6, timings of charge storage and reading of each row in the array of a plurality of pixels 54 are shown. In the line exposure mode, the light source control unit 33 causes the light source 32 to maintain a turned-on state.

In FIG. 6, a frame cycle based on a timing at which reading of pixel information of a previous frame is completed in the pixels 54 of the first row, i.e., a start timing of the available storage period, is shown. At time t1, the pixels 54 of the first row are reset. Thereby, the available storage period of the pixels 54 of the first row is started. During the available storage period, a signal based on light incident on the pixel 54 is stored.

At time t1, reading of pixel signals of the pixels 54 of the second row is started. The reading of the pixel signals includes a charge transfer and signal reading. Thereby, the available storage period of the pixels 54 of the second row ends and the pixels 54 of the second row output pixel signals. At time t2 when a predetermined time has elapsed from time t1, the reading of the pixel signals of the pixels 54 of the second row is completed and the pixels 54 of the second row are reset. Thereby, the available storage period of the pixels 54 of the second row is started.

At time t2, the reading of the pixel signals of the pixels 54 of the third row is started. Thereby, the available storage period of the pixels 54 of the third row ends and the pixels 54 of the third row output pixel signals. At time t3 when the predetermined time has elapsed from time t2, reading of the pixel signals of the pixels 54 of the third row is completed and the pixels 54 of the third row are reset. Thereby, the available storage period of the pixels 54 of the third row is started.

As in the above-described operation, pixel signals are read and reset in the pixels 54 of the fourth to eighth rows.

At time t4 when the pixels 54 of the eighth row are reset, the reading of the pixel signals of the pixels 54 of the first row is started. Thereby, the available storage period of the pixel 54 of the first row ends and the pixels 54 of the first row output pixel signals. At time t5 when a predetermined time has elapsed from time t4, the pixels 54 of the first row are reset. Thereby, the available storage period of the pixels 54 of the first row is started. Thereafter, the above-described operation is iterated.

At time t0 before time t1, the reading of the pixel signals of the pixels 54 of the first row is started. A length of a period from time t0 to time t4 is the same as the frame cycle. In the frame cycle, the reading of pixel signals of all the pixels 54 is sequentially performed row by row in an arrangement order of rows. A length of the period necessary for reading the pixel signals of all the pixels 54 is a shortest cycle in which imaging can be performed. The pixel signals read during a period from time t0 to time t4 constitute the image of the subject of one frame.

As described above, the pixel signals are read from the pixels 54 in the arrangement order of rows. In other words, an operation (a rolling shutter operation) of consecutively reading pixel signals from the pixels 54 of each row is iterated while the row to be read is shifted row by row. In the operation shown in FIG. 6, the imaging device control unit 30 causes the imaging device 21 to perform a second scan for reading the pixel signals from the pixels 54 in all of the plurality of rows by consecutively scanning all of the plurality of rows.

As shown in FIG. 6, according to the rolling shutter operation, charge storage is simultaneously performed in a plurality of pixels 54 of each row (line exposure) and reading of pixel signals is sequentially performed for each row. The pixels 54 of the row in which the reading of the pixel signals is completed are reset and charge storage is resumed.

Figure 7:
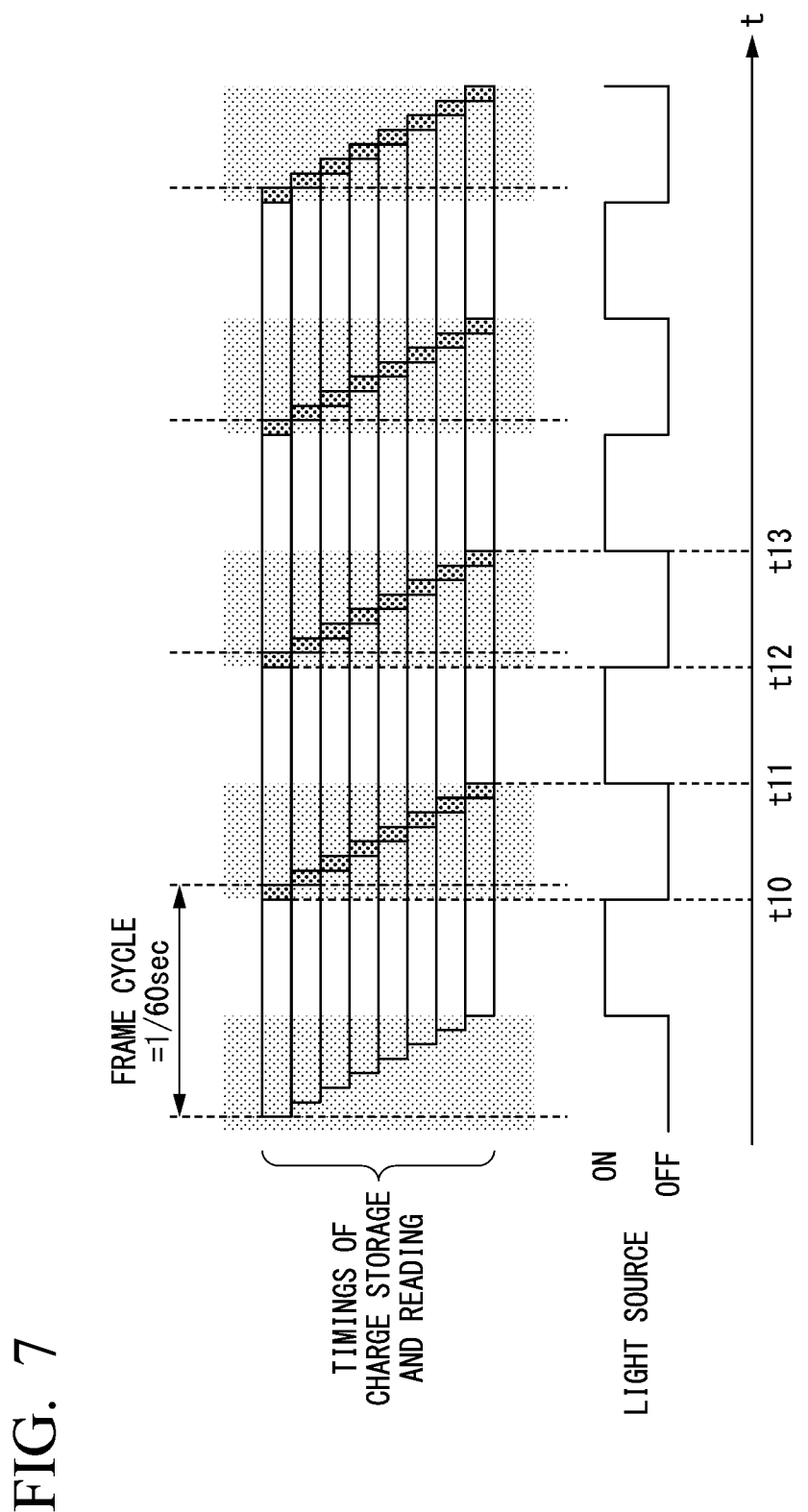
FIG. 7 is a timing chart showing operations of the imaging device and a light source in the first embodiment of the present invention.

FIG. 7 shows operations of the imaging device 21 and the light source 32 in the global exposure mode. In the upper-side drawing of FIG. 7, a horizontal direction indicates time and a vertical direction indicates a position of a row of the pixels 54 of the imaging device 21. In FIG. 7, the operations in the pixels 54 of eight rows are shown. A top row is a first row and a bottom row is an eighth row. In the lower-side drawing of FIG. 7, a lateral direction indicates time and a longitudinal direction indicates a state of the light source 32. "ON" indicates a state in which the light source 32 is turned on. "OFF" indicates a state in which the light source 32 is turned off.

In FIG. 7, a cycle of imaging, i.e., the frame cycle, is $\frac{1}{60}$ sec and a time required for reading the pixel signals of all the pixels 54 in the operation of each frame is about $\frac{1}{120}$ sec. In FIG. 7, timings of charge storage and reading of each row in the array of a plurality of pixels 54 are shown. In the global exposure mode, the light source 32 is intermittently turned on. The light source control unit 33 causes the light source 32 to be intermittently turned on.

In FIG. 7, a frame cycle based on a timing at which reading of pixel information of a previous frame is completed in the pixels 54 of the first row, i.e., a start timing of the available storage period, is shown. During a period from time t10 to time t11 shown in FIG. 7, an operation similar to an operation during a period from time t0 to time t4 shown in FIG. 6 is performed. In other words, during a period from time t10 to time t11, the reading of the pixel signals of all the pixels 54 is sequentially performed for each row. In the operation shown in FIG. 7, the imaging device control unit 30 causes the imaging device 21 to perform a second scan for reading the pixel signals from the pixels 54 in all of the plurality of rows by consecutively scanning all of the plurality of rows.

A period required for reading pixel signals of one frame is different between the operation shown in FIG. 6 and the operation shown in FIG. 7. In the operation shown in FIG. 6, the period necessary for reading pixel signals of one frame is the same as the frame cycle. In the operation shown in FIG. 7, the period necessary for reading the pixel signals of one frame is about half of the frame cycle. The pixel signals read during the period from time t10 to time t11 constitute the image of the subject of one frame. At time t10, the light source control unit 33 switches the light source 32 from the turned-on state to the turned-off state. During the period from time t10 to time t11, the light source control unit 33 causes the light source 32 to be turned off. At time t11, the light source control unit 33 switches the light source 32 from the turned-off state to the turned-on state.

After time t11, during a period from time t12 to time t13, an operation similar to an operation during the period from time t10 to time t11 is performed. During a period from time t11 to time t12, all the pixels 54 can simultaneously store charges. During the period from time t11 to time t12, the light source control unit 33 causes the light source 32 to be turned on. In other words, the light source 32 is turned on in a pulse form. During this period, global exposure is performed.

When the time required for reading the pixel signals of all the pixels 54 is shorter than the frame cycle, it is possible to secure a period during which all the pixels 54 can simultaneously store charges. In FIG. 7, the period during which all the pixels 54 can simultaneously store charges is about $\frac{1}{120}$ sec. As in an endoscope, in a camera inserted into a closed space and configured to perform imaging, pixels of the imager are not exposed while the illumination is turned off. Thus, it is possible to control an exposure time and an exposure timing by controlling turning-on and -off timings of the illumination. As shown in FIG. 7, it is possible to perform global exposure by performing turning-on control so that the light source 32 is turned off during a period in which pixel signals are read from the pixels 54 of each row and the light source 32 is turned on only during the period in which all the pixels 54 simultaneously store charges.

When the global exposure mode (a third mode) is set, the imaging device control unit 30 causes the imaging device 21 to perform the second scan during a period shorter than the frame cycle. The imaging device 21 generates an image (a third image) using the pixel signals read by the second scan in the global exposure mode. The light source control unit 33 causes the light source 32 to be turned on during a period including all or a part of a period during which the available storage periods of the pixels 54 in the plurality of rows overlap before the second scan in the global exposure mode is performed. The light source control unit 33 causes the light source 32 to be turned off during a period in which the second scan in the global exposure mode is performed.

At time t11 shown in FIG. 7, the reading of the pixel signals of the pixels 54 of the eighth row is completed. Thereafter, at time t12, the reading of the pixel signals of the pixels 54 of the first row is started. During a period from time t11 to time t12, available storage periods of the pixels 54 in the plurality of rows, i.e., all the pixels 54, overlap. The light source 32 is turned on during this period. In other words, in FIG. 7, the light source 32 is turned on during a period including all of a period during which the available storage periods of all the pixels 54 overlap. The light source 32 may be turned on in only a part of a period from time t11 to time t12. During the period from time t11 to time t12, all the pixels 54 are simultaneously exposed.

For example, the period during which the second scan is performed in the global exposure mode is less than or equal to half of the frame cycle. By increasing a driving frequency of an operation of reading the pixel signal of each pixel 54 to shorten a time required for the second scan, an available global exposure period that is a period during which the available storage periods of all the pixels 54 overlap becomes longer.

At time t12 shown in FIG. 7, the reading of the pixel signals of the pixels 54 of the first row is started. Thereafter, the pixel signals of the pixels 54 of each row are read by the second scan. The second scan is performed during a period from time t12 to time t13. During this period, the light source 32 is turned off. In other words, in FIG. 7, the light source 32 is turned off during a period in which the pixel signals of all the pixels 54 are read. The light source control unit 33 causes the light source 32 to be turned off at a timing when the reading of the pixel signal is started in the pixel 54 from which the pixel signal is read at the beginning of each frame. During a period in which the pixel signal of each pixel 54 is read, the light source control unit 33 causes the light source 32 to be maintained in the turned-off state.

Figure 8:
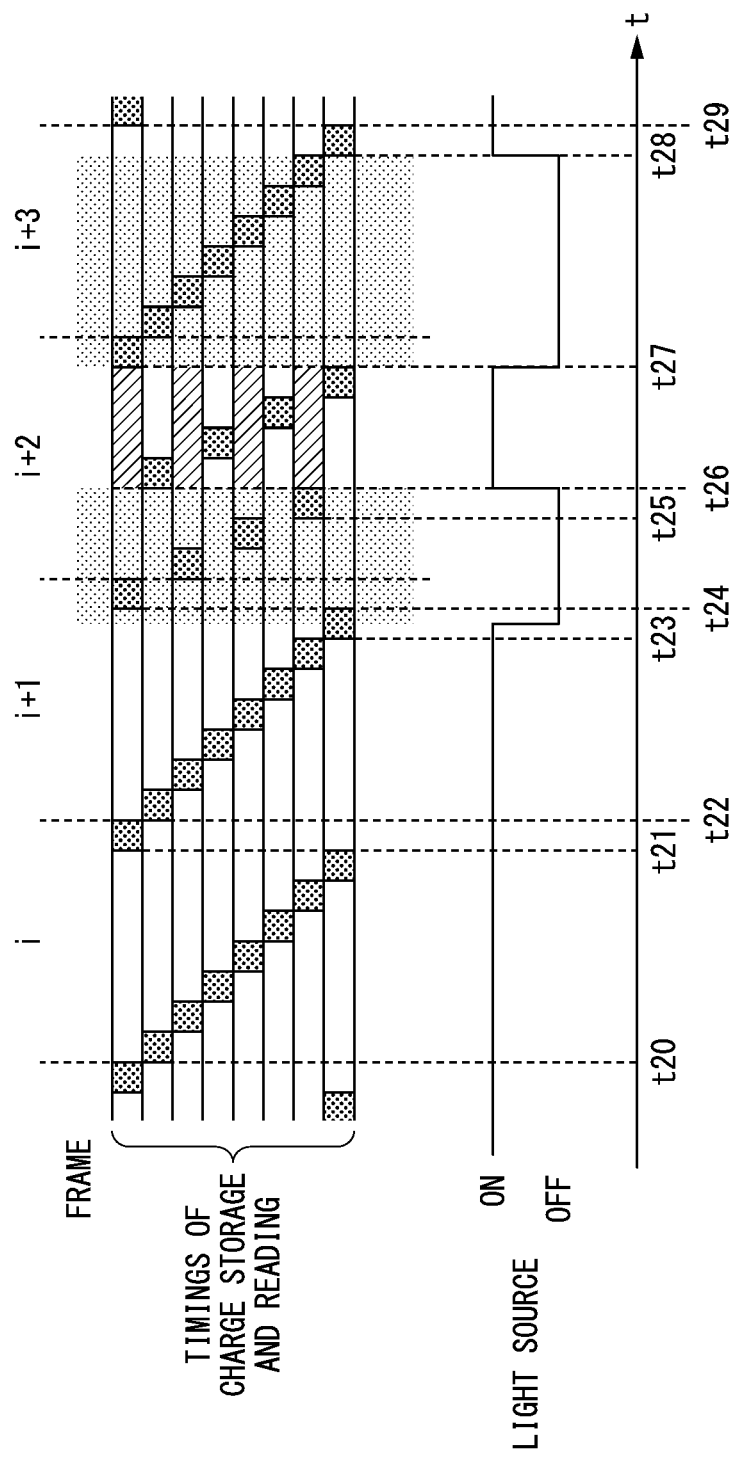
FIG. 8 is a timing chart showing the operations of the imaging device and the light source in the first embodiment of the present invention.

FIG. 8 shows operations of the imaging device 21 and the light source 32 in a mode in which line exposure and SG exposure are combined. In the upper-side drawing of FIG. 8, a horizontal direction indicates time and a vertical direction indicates a position of a row of the pixels 54 of the imaging device 21. In FIG. 8, the operations in the pixels 54 of eight rows are shown. A top row is a first row and a bottom row is an eighth row. In the lower-side drawing of FIG. 8, a lateral direction indicates time and a longitudinal direction indicates a state of the light source 32. "ON" indicates a state in which the light source 32 is turned on. "OFF" indicates a state in which the light source 32 is turned off.

In FIG. 8, timings of charge storage and reading of each row in the array of a plurality of pixels 54 are shown. The operation shown in FIG. 8 includes operations of four frames.

In FIG. 8, a frame cycle based on a timing at which reading of pixel information of a previous frame is completed in the pixels 54 of the first row, i.e., a start timing of the available storage period, is shown. In frame i, an operation in the line exposure mode that is the second mode is performed. The operation in frame i is similar to the operation shown in FIG. 6. When the line exposure mode is set, the imaging device control unit 30 causes the imaging device 21 to perform the second scan for reading pixel signals from pixels 54 in all of a plurality of rows by consecutively scanning all of the plurality of rows. When the line exposure mode is set, the light source control unit 33 causes the light source 32 to be turned on during a period including all of the available storage period of the pixels 54 in each of the plurality of rows before the second scan is performed. The imaging device 21 generates an image (a second image) using the pixel signals read by the second scan.

At time t21 shown in FIG. 8, reading of pixel signals of the pixels 54 of the first row is started. Thereafter, pixel signals of the pixels 54 of each row are read by the second scan. Reading of pixel signals of the pixels 54 of the eighth row starts at time t23 and ends at time t24. The pixel signals read from all the pixels 54 from time t21 to time t24 constitute an image of frame i (a second image). The display unit 5 displays the image of frame i.

In FIG. 8, during a period including at least a period from time t20 at which the available storage period of the pixels 54 of the first row starts to time t23 at which the available storage period of the pixels 54 of the eighth row ends, the light source control unit 33 causes the light source 32 to maintain the turned-on state.

Operations in frame i+1, frame i+2, and frame i+3 will be described. In frames i+1 to i+3, the operation in the SG exposure mode that is the first mode is performed. Frame i is a frame to be subjected to the line exposure and frame i+2 is a frame to be subjected to the SG exposure. In the operation shown in FIG. 8, the mode setting unit 343 sets the line exposure mode in the light source control unit 33 and the imaging device control unit 30 and then sets the SG exposure mode in the light source control unit 33 and the imaging device control unit 30.

After the available storage period of the pixels 54 of the first row of frame i+1 is started at time t22, the available storage periods of the pixels 54 of the rows are sequentially started in an arrangement order of rows. At time t24, the available storage period of the pixels 54 of the eighth row is started. When pixel signals generated by the pixels 54 in frame i+1 are read, an order of rows in which the pixel signals are read is different from an order in the line exposure mode. In other words, an order of rows to be scanned by the imaging device 21 is different from the arrangement order of rows that is an order in the line exposure mode. Specifically, pixel signals of pixels 54 of odd-numbered rows are first read. After reading of the pixel signals of the pixels 54 of the odd-numbered rows is completed, pixel signals of pixels 54 of even-numbered rows are read.

In the first embodiment, the simultaneous exposure lines are the odd-numbered rows. The simultaneous exposure lines are some of a plurality of rows in the array of the plurality of pixels 54. The simultaneous exposure lines include two or more rows. In frame i+2, pixels 54 of two or more rows that are the simultaneous exposure lines are simultaneously exposed. In other words, in frame i+2, exposure periods of the pixels 54 of two or more rows that are simultaneous exposure lines are the same. The even-numbered rows other than the simultaneous exposure lines are non-simultaneous exposure lines. The non-simultaneous exposure lines are rows other than the simultaneous exposure lines among a plurality of rows in the array of the plurality of pixels 54.

At time t24, reading of pixel signals of pixels 54 of the first row of frame i+1 is started. Thereby, the available storage period of the pixels 54 of the first row ends and the pixels 54 of the first row output pixel signals. At time t24, reading of the pixel signals of the pixels 54 of the simultaneous exposure lines is started. Thereafter, reading of the pixel signals of the pixels 54 of the simultaneous exposure lines are sequentially performed for each row. In other words, the pixel signals of the pixels 54 are sequentially read for each row of the odd-numbered rows in the array of the plurality of pixels 54. At time t25, reading of the pixel signals of the pixels 54 of a seventh row is started. Thereby, the available storage period of the pixels 54 of the seventh row ends. At time t26 when a predetermined time has elapsed from time t25, the reading of the pixel signals of the pixels 54 of the simultaneous exposure lines ends and the pixels 54 of the seventh row output pixel signals.

When the pixel signals constituting the image of frame i are read from the pixels 54, i.e., when the operation of the second scan is executed, the SG exposure mode is set. The imaging element control unit 30 causes the imaging element 21 to perform the first scan for reading pixel signals from the pixels 54 in the simultaneous exposure lines by consecutively scanning all the simultaneous exposure lines for reading of pixel signals constituting the image of frame i+1. During the period from time t24 to time t26, pixel signals constituting the image of frame i+1 are sequentially output from the pixels 54 in the simultaneous exposure lines by the first scan.

When the pixel signals constituting the image of frame i+1 are read from the pixels 54 in the simultaneous exposure lines, the light source 32 is turned off. When the SG exposure mode is set, the light source control unit 33 causes the light source 32 to be turned off during a period including all of the period during which the first scan is performed. In FIG. 8, during a period from time t23 to time t24, the light source control unit 33 switches the light source 32 from the turned-on state to the turned-off state. The light source 32 is turned off during a period including times t24 to t26. During a period from time t24 to time t26, pixel signals constituting the image of frame i+1 are read from the pixels 54 in all the simultaneous exposure lines. In FIG. 8, the light source 32 is turned off during a period including all of the period during which the first scan is performed.

The pixels 54 in the simultaneous exposure lines on which the first scan is performed are reset when reading of pixel signals is completed. According to the resetting, the available storage period of the pixels 54 of frame i+2 in the simultaneous exposure lines is started. By intermittently turning the light source 32 on after the pixels 54 in all the simultaneous exposure lines are reset, the exposure periods of frame i+2 of the pixels 54 in the simultaneous exposure lines can be made the same. In other words, when the pixel signals of frame i+2 of the pixels 54 in the simultaneous exposure lines are generated, it is possible to perform exposure (SG exposure) without rolling distortion. The period from time t26 to time t27 is the available SG exposure period. During the available SG exposure period, the available storage periods of the pixels 54 in all the simultaneous exposure lines of the frame to be subjected to the SG exposure overlap.

When the SG exposure mode is set, the light source control unit 33 causes the light source 32 to be turned on during a period of all or a part of the available SG exposure period. Specifically, after scanning of all the simultaneous exposure lines is completed by the first scan for a frame previous to a frame to be subjected to the SG exposure, the light source control unit 33 causes the light source 32 to be turned on. The light source 32 is turned on during a period including all or a part of a period during which the available storage periods of the pixels 54 in all the simultaneous exposure lines of the frame to be subjected to the SG exposure overlap. The imaging device 21 generates an image (a first image) using pixel signals generated by the pixels 54 in all the simultaneous exposure lines when the light source 32 is turned on during the period. The period includes all or a part of a period during which the available storage periods of the pixels 54 in all the simultaneous exposure lines of the frame to be subjected to the SG exposure overlap.

At time t26 shown in FIG. 8, reading of pixel signals of the pixels 54 of frame i+1 of the seventh row that is the simultaneous exposure line is completed. Thereafter, at time t27, reading of pixel signals of the pixels 54 of frame i+2 of the first row that is the simultaneous exposure line is started. During a period from time t26 to time t27, the available storage periods of frame i+2 of the pixels 54 in all the simultaneous exposure lines overlap. The light source 32 is turned on during this period. In other words, in FIG. 8, the light source 32 is turned on during a period including all periods during which the available storage periods of frame i+2 of the pixels 54 in all the simultaneous exposure lines overlap. At time t26, the light source control unit 33 switches the light source 32 from the turned-off state to the turned-on state. The light source 32 may be turned on in only a part of the period from time t26 to time t27. During the period from time t26 to time t27, the pixels 54 in all the simultaneous exposure lines are simultaneously exposed. During the period from time t26 to time t27, the pixels 54 in the simultaneous exposure lines are subjected to exposure of frame i+2.

The light source control unit 33 causes the light source 32 to be turned on at a timing at which the available storage period is started in the pixels 54 in which the charge storage of frame i+2 finally starts among the pixels 54 of the simultaneous exposure lines. Alternatively, the light source control unit 33 causes the light source 32 to be turned on after a timing at which the available storage period is started in the pixels 54 in which the charge storage of frame i+2 finally starts among the pixels 54 of the simultaneous exposure lines. As shown in FIG. 8, the pixels 54 in which the charge storage of frame i+2 finally starts among the pixels 54 of the simultaneous exposure lines are the pixels 54 of the seventh row. The light source control unit 33 controls a turning-on timing of the light source 32 so that the next time until the light source 32 is turned off is an exposure time that is determined to be appropriate by the image processing unit 31. According to this control, it is possible to avoid saturation of the pixel signals of the pixels 54 in a scene in which pixel signals of pixels 54 of all or some of the simultaneous exposure lines are saturated when the light source 32 is turned on in all of the available SG exposure period.

As described above, during the period from time t24 to time t26, the pixel signals constituting the image of frame i+1 are read from the pixels 54 in all the simultaneous exposure lines by the first scan. Thereafter, during the period in which the available storage periods of the pixels 54 in all the simultaneous exposure lines overlap, the imaging device control unit 30 causes the imaging device 21 to perform a scan for reading pixel signals from the pixels 54 in the non-simultaneous exposure lines. Thereby, pixel signals constituting the image of frame i+1 are read from the pixels 54 in the non-simultaneous exposure lines. During the period from time t26 to time t27 shown in FIG. 8, the pixel signals of the pixels 54 of the even-numbered rows that are non-simultaneous exposure lines are read.

An exposure time of the pixels 54 of each row in frame i+1 is different. Thus, the display processing unit 341 controls the image processing unit 31 so that the image processing unit 31 does not output a video signal constituting the image of frame i+1 to the display unit 5. The display unit 5 does not display the image of frame i+1.

Pixel signals of frame i+1 (a first frame) are read from the pixels 54 in all the simultaneous exposure lines by the first scan and pixel signals of frame i+1 are further read from the pixels 54 in the non-simultaneous exposure lines. Thereafter, the imaging device control unit 30 causes the imaging device 21 to read the pixel signals of frame i+2 (a second frame) from all the pixels 54 in the rows including all the simultaneous exposure lines. The imaging device 21 generates an image (the first image) using the pixel signals of frame i+2. The light source control unit 33 causes the light source 32 to be turned off during a period including all of a period during which a scan is performed for reading pixel signals generated by the pixels 54 in all simultaneous exposure lines from the pixels 54. In other words, the light source control unit 33 causes the light source 32 to be turned off during the period in which the pixel signals of frame i+2 are read from the pixels 54 in the simultaneous exposure lines.

When the pixel signals generated by the pixels 54 are read in frame i+2 and frame i+3, an order of rows in which the pixel signals are read is the same as the order in the line exposure mode. At time t27 shown in FIG. 8, reading of the pixel signals of the pixels 54 of the first row is started. Thereafter, pixel signals of the pixels 54 of each row are read by the second scan. The reading of the pixel signals of the pixels 54 of the eighth row starts at time t28 and ends at time t29. The pixel signals read from all pixels 54 from time t27 to time t29 constitute the image of frame i+2.

The image of frame i+2 is used by the rolling distortion determination unit 342. The exposure time of the pixels 54 of each non-simultaneous exposure line in frame i+2 differs according to each non-simultaneous exposure line. Thus, the display processing unit 341 controls the image processing unit 31 so that a video signal constituting the image of frame i+2 is not output to the display unit 5. The display unit 5 does not display the image of frame i+2. Therefore, the display unit 5 displays only the image of frame i between the image of frame i+2 (the first image) and the image of frame i (the second image).

As described above, when the global exposure mode is set, the imaging device control unit 30 causes the imaging device 21 to perform the second scan during a period shorter than the frame cycle. The imaging device 21 generates a third image using the pixel signals read by the second scan in the global exposure mode. The display unit 5 may display only the image of frame i and the third image among the image of frame i+2 (the first image), the image of frame i (the second image), and the third image.

At time t27 shown in FIG. 8, reading of the pixel signals of the pixels 54 of the first row is started. Thereafter, at time t28, reading of the pixel signals of the pixels 54 of the eighth row is started. During a period from time t27 to time t28, pixel signals of all pixels 54 including the simultaneous exposure lines are read. The light source 32 is turned off during this period. In other words, in FIG. 8, the light source 32 is turned off during a period including a period during which the pixel signals of frame i+2 of the pixels 54 in the rows including all the simultaneous exposure lines are read. At time t27, the light source control unit 33 switches the light source 32 from the turned-on state to the turned-off state. The light source control unit 33 causes the light source 32 to be turned off at a timing when the reading of pixel signals of frame i+2 has been started in a pixel 54 from which the pixel signal is first read among the pixels 54 of the simultaneous exposure lines. During a period in which the pixel signals of the pixels 54 of the simultaneous exposure lines are read, the light source control unit 33 causes the light source 32 to be maintained in the turned-off state.

After time t28, at time t29, reading of the pixel signals of the pixels 54 of the first row is started. Thereafter, pixel signals of the pixels 54 of each row are read by the second scan. The pixel signals read from all the pixels 54 by this second scan constitute the image of frame i+3. The exposure time of the pixels 54 of each row in frame i+3 differs according to each row. Thus, the display processing unit 341 controls the image processing unit 31 so that the video signal constituting the image of frame i+3 is not output to the display unit 5. The display unit 5 does not display the image of frame i+3.

The light source control unit 33 causes the light source 32 to be turned on after reading of a pixel signal of the pixel 54 in which charge storage of frame i+2 finally starts is completed and during a period until an available charge storage period of the pixel 54 in which charge storage of frame i+4 initially starts is started. At time t28 shown in FIG. 8, the light source control unit 33 switches the light source 32 from the turned-off state to the turned-on state.

In frame i+2, during a period (a period from time t26 to time t27) other than the period during which the pixel signals of frame i+1 are read from the pixels 54 in all the simultaneous exposure lines by the first scan, all the pixels 54 in the simultaneous exposure lines can be exposed at the same time. During a period in which all the pixels 54 in the simultaneous exposure lines are simultaneously exposed, the pixel signals of frame i+1 are read from the pixels 54 in all non-simultaneous exposure lines.

In FIG. 8, the simultaneous exposure lines or the non-simultaneous exposure lines are four rows, i.e., the number of simultaneous exposure lines or the number of non-simultaneous exposure lines is half of the total number of rows of the pixels 54 of the imaging device 21. Thus, the exposure time of the pixels 54 in the simultaneous exposure lines is half of the frame cycle. If the simultaneous exposure lines are more than 4 rows, the non-simultaneous exposure lines are less than 4 rows. In this case, the exposure time of the pixels 54 in the simultaneous exposure lines is shorter than half of the frame cycle. If the simultaneous exposure lines are less than 4 rows, the non-simultaneous exposure lines are more than 4 rows. In this case, the exposure time of the pixels 54 in the simultaneous exposure lines can be made longer than half of the frame cycle. When the SG exposure mode is set, the light source control unit 33 controls a turning-on time of the light source 32 in accordance with the number of simultaneous exposure lines.

In the operation of each frame shown in FIG. 8, a time required for reading the pixel signals of all the pixels 54 is the same as the frame cycle. Thus, high-speed reading driving is unnecessary.

Although the simultaneous exposure line is an odd-numbered row as shown in FIG. 8, the simultaneous exposure line may be an even-numbered row. A group of simultaneous exposure lines may be formed of n consecutive rows and n rows that are non-simultaneous exposure lines may be disposed between two groups. n is an integer of 2 or more. For example, when n is 2, the simultaneous exposure lines are first and second rows, fifth and sixth rows, ninth and tenth rows, and the like.

The operation of the endoscope apparatus 1 in accordance with the temperature will be described. In a situation where the temperature around the distal end 20 of the insertion unit 2 is high, the temperature of the imaging device 21 becomes extremely high, so that the imaging device 21 or its peripheral part may be likely to break down. Thus, in a situation in which the temperature is high, a user is notified of a warning. When the temperature measured by the temperature sensor 23 is higher than a first threshold value, the display unit 5 displays a warning. For example, the first threshold value is 80° C. Specifically, when the temperature is higher than the first threshold value, the display processing unit 341 generates graphic data for displaying the warning. The graphic data generated by the display processing unit 341 is output to the image processing unit 31. The image processing unit 31 generates a video signal for display by synthesizing image data on which image processing has been performed with the graphic data. The display unit 5 displays the warning on the basis of the video signal output from the image processing unit 31. Thereby, the endoscope apparatus 1 prompts the user to stop inspection.

The operation of the endoscope apparatus 1 when the temperature measured by the temperature sensor 23 is less than or equal to the first threshold value will be described. The mode setting unit 343 performs switching between settings of the SG exposure mode (the first mode), the line exposure mode (the second mode), and the global exposure mode (the third mode) for the light source control unit 33 and the imaging device control unit 30. When the temperature is higher than a second threshold value (a predetermined value), the mode setting unit 343 sequentially sets the SG exposure mode and the line exposure mode in the light source control unit 33 and the imaging device control unit 30. When the temperature is less than or equal to the second threshold value, the mode setting unit 343 sets the global exposure mode in the light source control unit 33 and the imaging device control unit 30.

The second threshold value is less than the first threshold value. For example, the second threshold value is 60° C. The mode setting unit 343 determines the temperature indicated by temperature data output from the temperature sensor 23 and performs switching between the setting of the SG exposure mode, the line exposure mode, and the global exposure mode in accordance with the temperature. When the temperature is less than or equal to the first threshold value and greater than the second threshold value, an operation in which the SG exposure mode and the line exposure mode are combined is performed. In other words, the operation shown in FIG. 8 is performed. Thereby, an image for detecting occurrence of rolling distortion is acquired. Also, heat generation in the imaging device 21 is reduced as compared with when the endoscope apparatus 1 operates in the global exposure mode. When the temperature is less than or equal to the second threshold value, the operation of the global exposure mode is performed. In other words, the operation shown in FIG. 7 is performed. Thereby, an image without rolling distortion is acquired.

Figure 9:
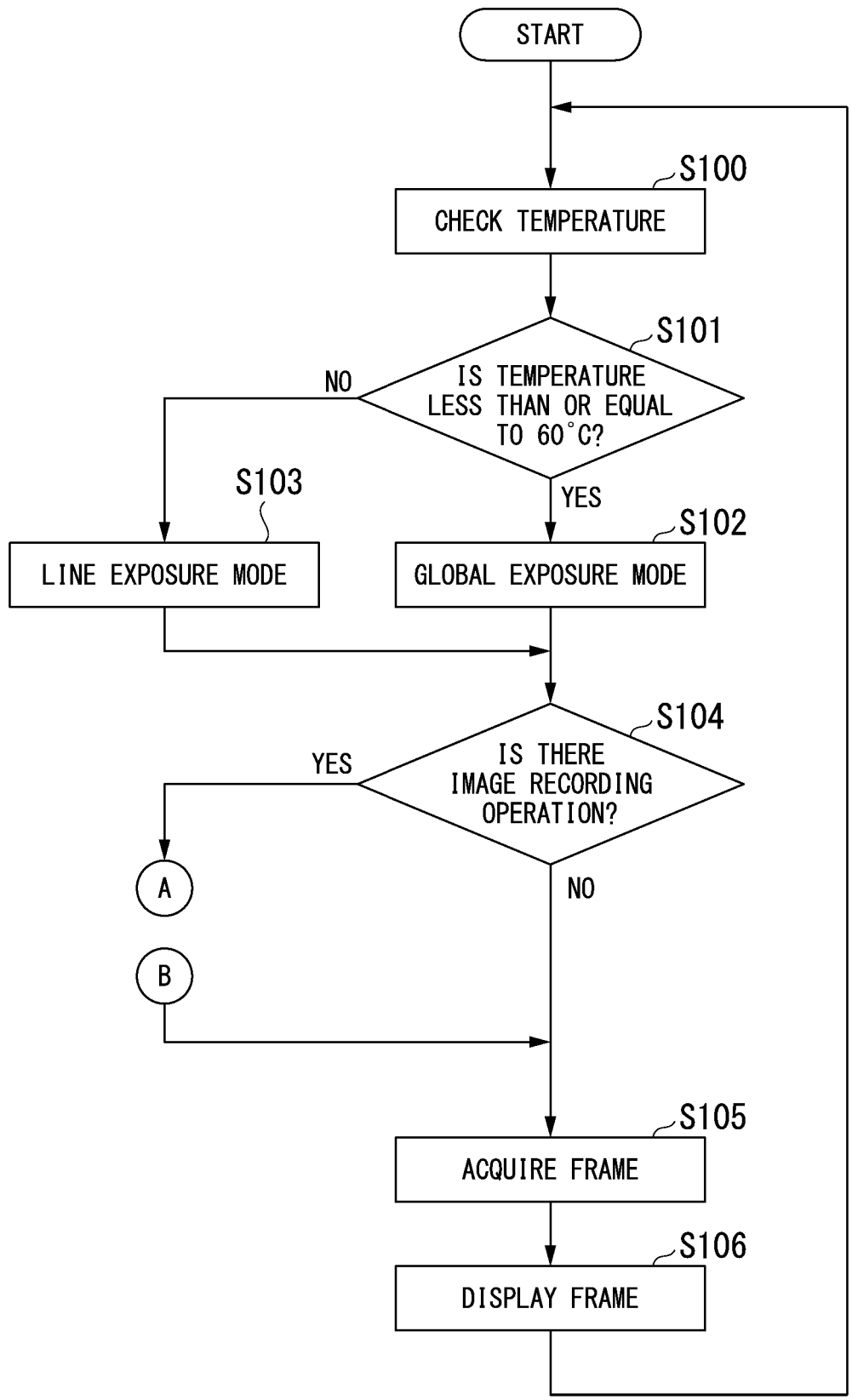
FIG. 9 is a flowchart showing an operation of the endoscope apparatus according to the first embodiment of the present invention.
Figure 10:
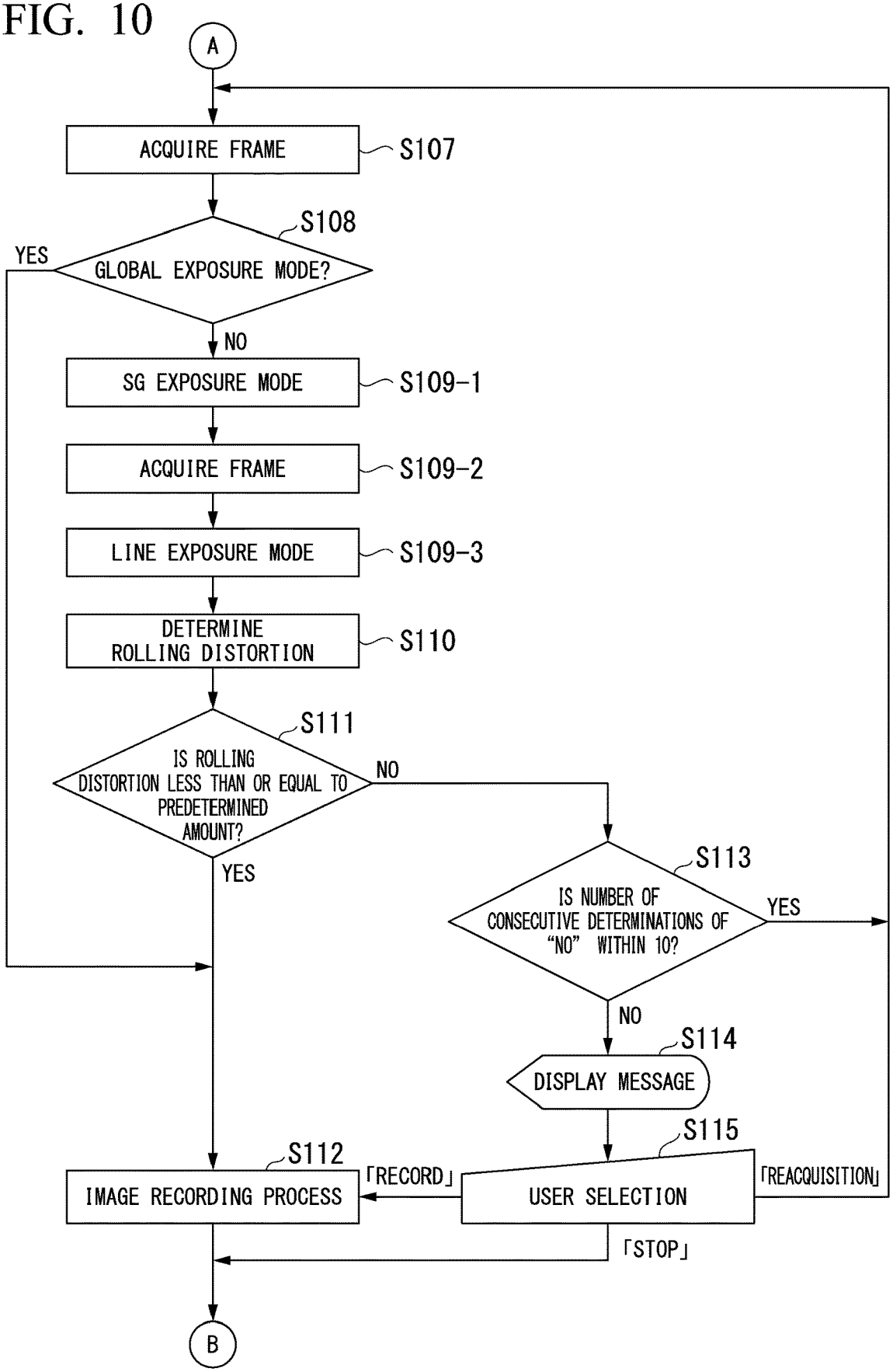
FIG. 10 is a flowchart showing an operation of the endoscope apparatus according to the first embodiment of the present invention.

FIGS. 9 and 10 show the operation of the endoscope apparatus 1 when the temperature measured by the temperature sensor 23 is less than or equal to the first threshold value. The operation of the endoscope apparatus 1 will be described with reference to FIGS. 9 and 10. FIGS. 9 and 10 correspond to the image recording process. The display unit 5 consecutively displays images of the subject. The user performs an image recording operation by operating the operation unit 4 at a timing at which an image is desired to be recorded. The user can input an image recording instruction to the endoscope apparatus 1 by an image recording operation. Also, the image recording instruction may be automatically generated inside the endoscope apparatus 1 at fixed time intervals. Alternatively, the image recording instruction may be given from another device outside the endoscope apparatus 1 by further adding a radio transmission/reception unit to the endoscope apparatus 1.

The mode setting unit 343 checks a temperature indicated by the temperature data output from the temperature sensor 23 (step S100).

After step S100, when it is determined that the temperature is 60° C. or less (step S101), the mode setting unit 343 sets the global exposure mode in the light source control unit 33 and the imaging device control unit 30 (step S102). After step S100, when it is determined that the temperature is not 60° C. or less (step S101), the mode setting unit 343 sets the line exposure mode in the light source control unit 33 and the imaging device control unit 30 (step S103).

After step S102 or S103, the control unit 340 determines whether or not an image recording operation has been performed on the basis of a signal from the operation unit 4 (step S104). In step S104, if the control unit 340 determines that an image recording operation has not been performed, an image of one frame is acquired (step S105). The operation in step S105 varies with the mode set in the light source control unit 33 and the imaging device control unit 30.

When the global exposure mode is set, pixel signals of one frame are acquired by the operation shown in FIG. 7. When the line exposure mode is set, pixel signals of one frame are acquired by the operation shown in FIG. 6 (step S105).

After step S105, the display unit 5 displays an image of one frame (step S106). After step S106, the processing in step S100 is performed. When the image recording operation is not performed by the user, the operation of the global exposure mode or the line exposure mode is iterated.

In step S104, when the control unit 340 determines that the image recording operation has been performed, an image of one frame is acquired according to the mode set in the light source control unit 33 and the imaging device control unit 30. In other words, the image of frame i shown in FIG. 8 is acquired (step S107).

After step S107, when the mode set in the light source control unit 33 and the imaging device control unit 30 is the global exposure mode (step S108), the recording unit 344 records the image acquired in step S107 in the memory 35 (step S112). After step S112, the processing in step S105 is performed. When the processing in step S112 is performed, the mode setting unit 343 sets the line exposure mode in the light source control unit 33 and the imaging device control unit 30 if the SG exposure mode is set in the light source control unit 33 and the imaging device control unit 30. Thereafter, the processing in step S105 is performed.

After step S107, when the mode set in the light source control unit 33 and the imaging device control unit 30 is not the global exposure mode (step S108), the mode setting unit 343 sets the SG exposure mode in the light source control unit 33 and the imaging device control unit 30 (step S109-1). Next, an image of one frame is acquired in accordance with the mode set in the light source control unit 33 and the imaging device control unit 30. In other words, the image of frame i+2 shown in FIG. 8 is acquired (step S109-2). Thereafter, the mode setting unit 343 sets the line exposure mode in the light source control unit 33 and the imaging device control unit 30 (step S109-3). Although the image of frame i+1 is acquired before the image of frame i+2 shown in FIG. 8 is acquired, the processing related to this operation is not shown in FIG. 10. Also, after the image of frame i+2 shown in FIG. 8 is acquired, the image of frame i+3 is acquired, but the processing related to this operation is not shown in FIG. 10.

After step S109-3, the rolling distortion determination unit 342 determines the situation of the occurrence of the rolling distortion using a first image and a second image. Specifically, the rolling distortion determination unit 342 compares data of the simultaneous exposure lines of the first image with data of rows corresponding to the simultaneous exposure lines of the first image in the second image. Thereby, the rolling distortion determination unit 342 determines the situation of the occurrence of the rolling distortion (step S110). The image generated by the pixels 54 in the simultaneous exposure lines is obtained by the processing in step S109-2. The pixel signals read by the second scan are obtained by the processing in step S107. When odd-numbered rows are simultaneous exposure lines, data of the odd-numbered rows in the two frame images are used. In the two frame images, the data of the same rows are compared.

A method of determining the rolling distortion will be described. The rolling distortion determination unit 342 extracts data of the simultaneous exposure line in the first image acquired in step S109-2. The extracted data constitutes a reference image. Further, the rolling distortion determination unit 342 extracts data of rows corresponding to the simultaneous exposure lines of the first image from the second image acquired in step S107. The extracted data constitutes a partial image. After geometric distortion of the reference image and the partial image is corrected, the rolling distortion determination unit 342 performs a process of extracting feature points in each image. The rolling distortion determination unit 342 associates feature points in the reference image and the partial image. The rolling distortion determination unit 342 calculates a motion vector of each feature point.

Figure 11A:
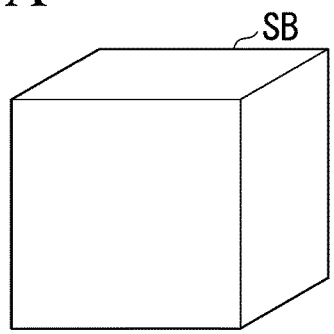
FIG. 11A is a reference diagram showing an image of a subject in the first embodiment of the present invention.
Figure 11B:
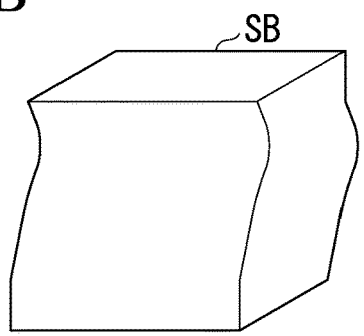
FIG. 11B is a reference diagram showing an image of the subject in the first embodiment of the present invention.

FIGS. 11A to 11D show images after geometric distortion of the reference image and the partial image of the subject SB is corrected. In FIGS. 11A to 11D, a background image of the subject SB is omitted. For simplification of description, a structure of the subject SB is a cube. FIG. 11A shows an image of the subject SB in the reference image. Rolling distortion does not occur in the reference image. FIG. 11B shows an image of the subject SB in the partial image. The rolling distortion occurs in the partial image, so that the subject SB is distorted.

Figure 11C:
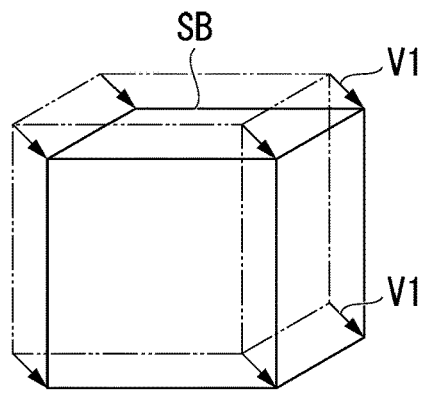
FIG. 11C is a reference diagram showing an image of the subject in the first embodiment of the present invention.

FIG. 11C shows the image of the subject SB in the partial image in which the rolling distortion has not occurred. In FIG. 11C, the subject SB moves parallel to the distal end 20 or the distal end 20 moves parallel to the subject SB, so that the image of the subject SB moves in parallel in a predetermined direction. A broken line in FIG. 11C shows the subject SB before movement. Directions and magnitudes of all the motion vectors V1 are the same.

Figure 11D:
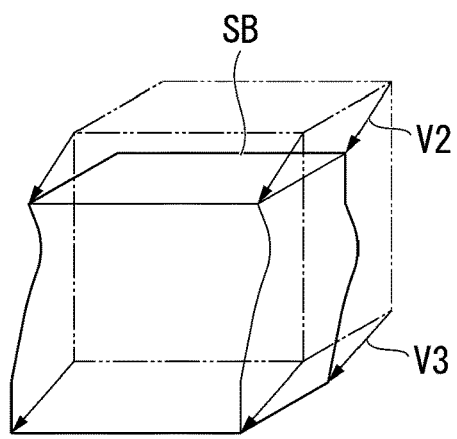
FIG. 11D is a reference diagram showing an image of the subject in the first embodiment of the present invention.

FIG. 11D shows an image of the subject SB in the partial image in which the rolling distortion occurs. A broken line in FIG. 11D shows the subject SB before the movement. Directions and magnitudes of a motion vector V2 at an upper part of the subject SB and a motion vector V3 at a lower part of the subject SB are different.

When variations in directions of all motion vectors are less than or equal to a third threshold value and variations in magnitudes of all the motion vectors are equal to or smaller than a fourth threshold value (FIG. 11C), the rolling distortion determination unit 342 determines that there is no rolling distortion. In other cases (FIG. 11D), the rolling distortion determination unit 342 determines that there is rolling distortion. When it is determined that there is rolling distortion, the rolling distortion determination unit 342 may determine an amount of occurrence of rolling distortion finely. For example, when the variations in the directions of all the motion vectors are greater than the third threshold value and less than or equal to a fifth threshold value and the variations in the magnitudes of all the motion vectors are greater than the fourth threshold value and less than or equal to a sixth threshold value, the rolling distortion determination unit 342 may determine that the rolling distortion is small. Alternatively, when the variations in the directions of all the motion vectors are greater than the fifth threshold value or when the variations in the magnitudes of all the motion vectors are greater than the sixth threshold value, the rolling distortion determination unit 342 may determine that the rolling distortion is large. A standard deviation or variance may be used as an index indicating the variation in the direction and magnitude of the motion vector or a difference between the maximum value and the minimum value may be used as the index.

When the rolling distortion determined in step S110 is less than or equal to a predetermined amount (step S111), the processing in step S112 is performed. In other words, when there is no rolling distortion or the rolling distortion is small, the processing in step S112 is performed. Therefore, after the image recording instruction is accepted, the recording unit 344 records the image (the second image) in which the rolling distortion determination unit 342 determines that the rolling distortion is less than or equal to the predetermined amount in the memory 35. The image acquired in step S107 is recorded in the memory 35. Thereby, it is possible to record an image with small rolling distortion. After step S112, the processing in step S105 is performed.

When the rolling distortion determined in step S110 is greater than the predetermined amount (step S111), the rolling distortion determination unit 342 checks the number of times the rolling distortion is consecutively determined to be greater than the predetermined amount (step S113). For example, a counter may be used to indicate the number of times the rolling distortion is consecutively determined to be greater than the predetermined amount. When the number of times the rolling distortion is consecutively determined to be greater than the predetermined amount in step S113 is within 10, the processing in step S107 is performed. In other words, when a situation in which the rolling distortion is greater than the predetermined amount continues, the image acquisition in steps S107 and S109-2 is iterated. In this case, the imaging device 21 iteratively generates an image (a first image) using the pixel signals generated by the pixels 54 in all the simultaneous exposure lines when the light source 32 is turned on and an image (a second image) using the pixel signals read by the second scan.

In step S113, when the number of times the rolling distortion is consecutively determined to be greater than the predetermined amount is greater than 10, the display processing unit 341 generates graphic data for displaying a message. The graphic data generated by the display processing unit 341 is output to the image processing unit 31. The image processing unit 31 generates a video signal for display by synthesizing the image data on which image processing has been performed with the graphic data. The display unit 5 displays a message based on the video signal output from the image processing unit 31 (step S114). Thereby, the display unit 5 displays a situation of occurrence of the rolling distortion determined by the rolling distortion determination unit 342.

Figure 12:
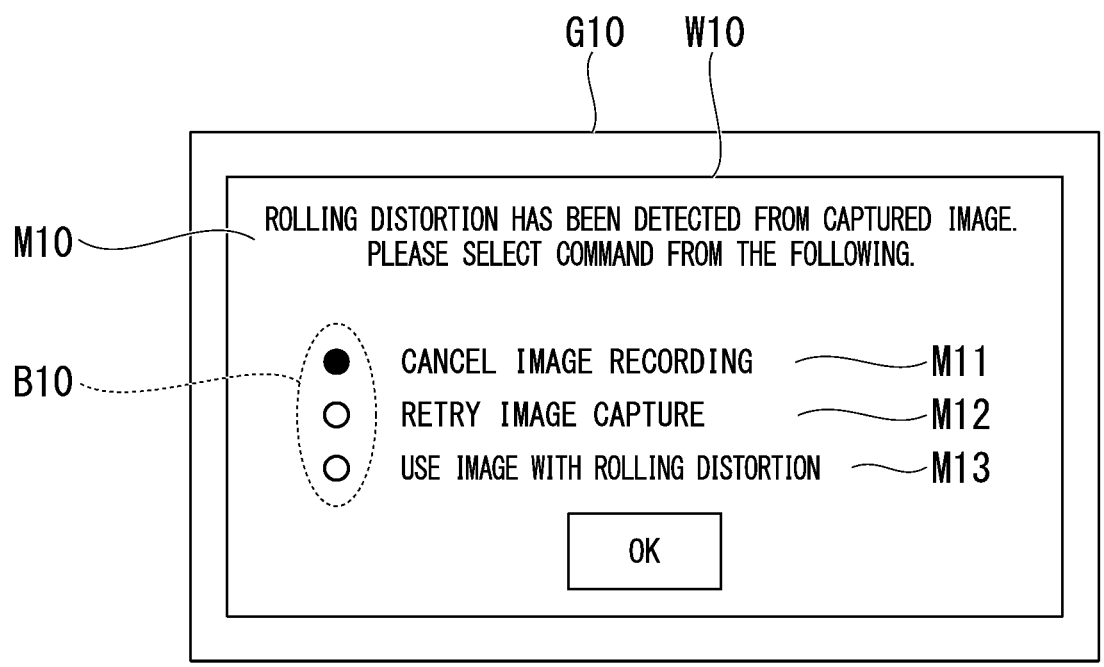
FIG. 12 is a reference diagram showing an image displayed on a display unit in the first embodiment of the present invention.

FIG. 12 shows an image G10 displayed by the display unit 5 in step S114. The image G10 includes a window W10. The window W10 includes a message M10 indicating the situation of the occurrence of the rolling distortion. Further, the window W10 includes a message M11, a message M12, and a message M13 for allowing the user to select a countermeasure. The message M11 indicates the stopping of the image recording process. The message M12 indicates image reacquisition. The message M13 indicates the recording of an image including rolling distortion. Further, the window W10 includes a check box B10 provided in correspondence with each message. When a situation in which large rolling distortion occurs continues, the endoscope apparatus 1 prompts the user to reacquire the image. The user operates the operation unit 4 to input a selection result into the check box B10 (step S115).

When the user selects to stop the image recording in step S115, the processing in step S105 is performed. In other words, when the method corresponding to the message M11 is selected, the processing in step S105 is performed. Because the SG exposure mode is set in the light source control unit 33 and the imaging device control unit 30, the mode setting unit 343 sets the line exposure mode in the light source control unit 33 and the imaging device control unit 30. Thereafter, the processing in step S105 is performed.

When the image reacquisition is selected by the user in step S115, the processing in step S107 is performed. In other words, when the method corresponding to the message M12 is selected, the processing in step S107 is performed. By reacquiring the image, there is a possibility that an image with small rolling distortion can be acquired.

When image recording is selected by the user in step S115, the processing in step S112 is performed. In other words, when the method corresponding to the message M13 is selected, the processing in step S112 is performed. In this case, in step S112, the recording unit 344 records the image whose rolling distortion is determined to be greater than the predetermined amount by the rolling distortion determination unit 342 in the memory 35. The image acquired in step S107 is recorded in the memory 35.

The threshold value used for the determination in step S113 may be a number other than 10. Also, the index used for the determination in step S113 may be an elapsed time from a timing at which it is determined that the image recording operation is performed in step S104. In this case, in step S113, it is determined whether or not the elapsed time is within, for example, 1 sec.

The processing from step S114 to step S115 and the processing from step S107 to step S111 may be parallelized. In other words, after the message M12 is displayed in the processing in step S114, the processing in steps S107 to S111 may be iterated until the user performs selection in the processing in step S115. In this case, when it is determined that the rolling distortion is less than the predetermined amount in step S111, a process is performed to switch the display to another message informing that an image with small rolling distortion can be acquired. Thereafter, the processing in step S112 is performed.

Figure 13:
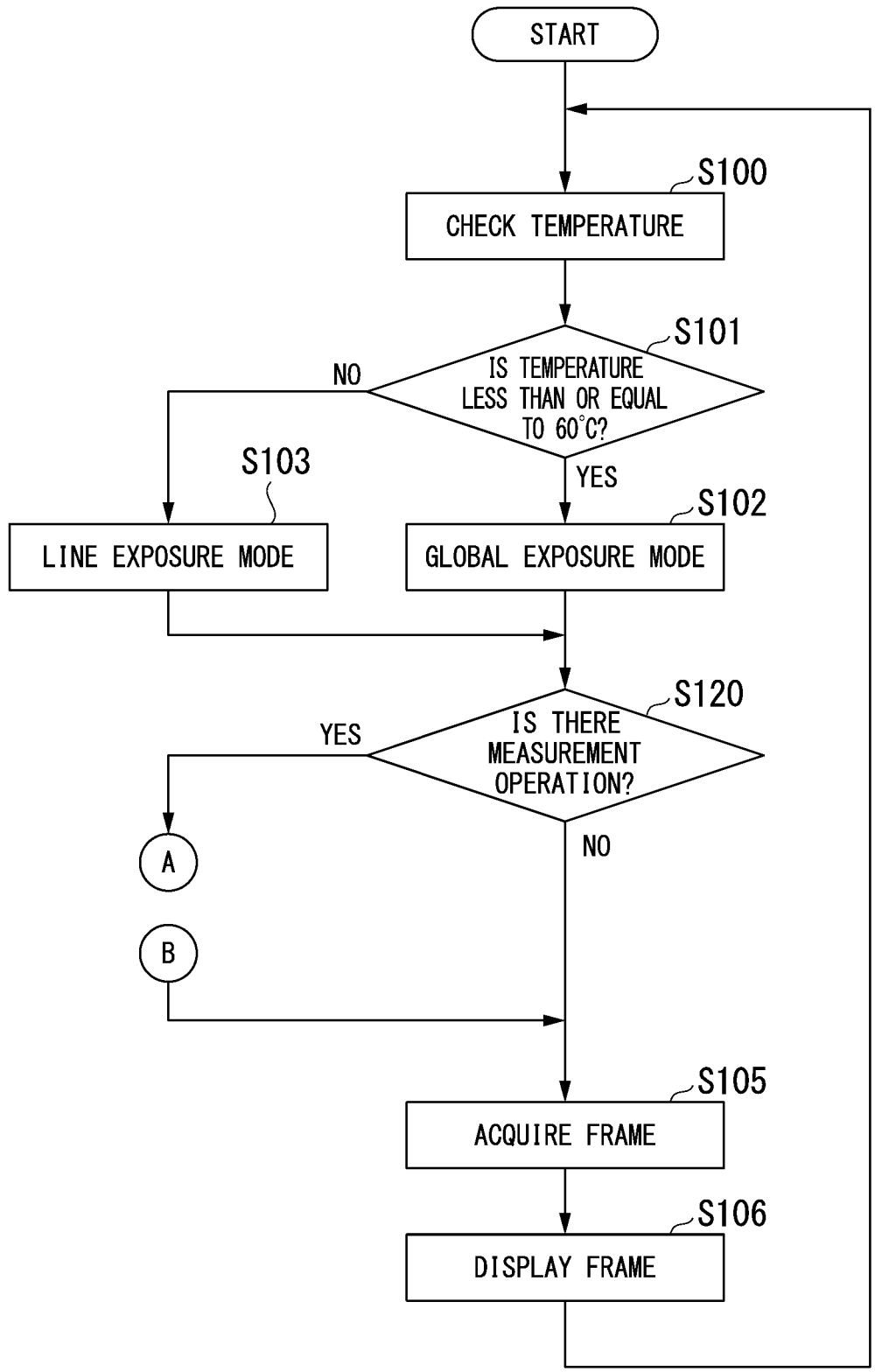
FIG. 13 is a flowchart showing an operation of the endoscope apparatus according to the first embodiment of the present invention.
Figure 14:
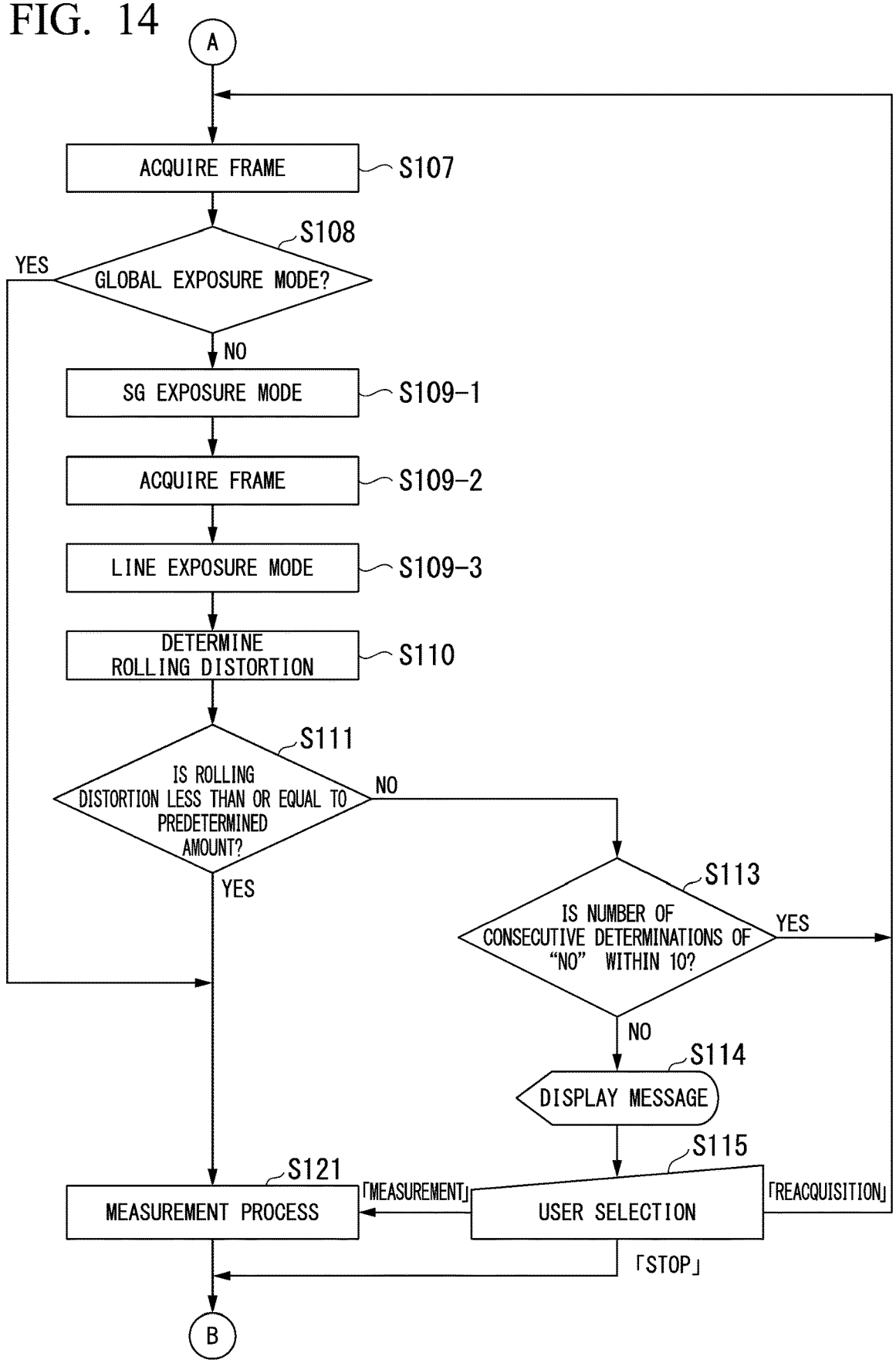
FIG. 14 is a flowchart showing an operation of the endoscope apparatus according to the first embodiment of the present invention.

FIGS. 13 and 14 show other operations of the endoscope apparatus 1 when the temperature measured by the temperature sensor 23 is less than or equal to the first threshold value. The operation of the endoscope apparatus 1 will be described with reference to FIGS. 13 and 14. FIG. 13 and FIG. 14 correspond to a measurement process. The display unit 5 consecutively displays images of the subject. The user performs a measurement operation by operating the operation unit 4 at a timing at which an image is desired to be recorded. The user can input a measurement instruction to the endoscope apparatus 1 by the measurement operation. With respect to the processes shown in FIGS. 13 and 14, differences from the processes shown in FIGS. 9 and 10 will be described.

Step S104 shown in FIG. 9 is changed to step S120. On the basis of a signal from the operation unit 4, the control unit 340 determines whether or not a measurement operation has been performed (step S120). In step S120, if the control unit 340 determines that the measurement operation has been performed, the processing in step S107 is performed. When the control unit 340 determines that the measurement operation is not performed in step S120, the processing in step S105 is performed.

Step S112 shown in FIG. 10 is changed to step S121. The measurement unit 345 performs a measurement process (step S121). In the measurement process, the measurement unit 345 calculates three-dimensional coordinates of measurement points designated by the user. The measurement unit 345 measures dimensions of the subject on the basis of the three-dimensional coordinates of each measurement point. For example, the measurement unit 345 measures at least one of a distance between two points, a length from the measurement point to a reference line, an area of a region, and the circumference of the region. When the rolling distortion determined in step S110 is less than or equal to the predetermined amount (step S111), an image with small rolling distortion is used for the measurement process in step S121. In other words, after the measurement instruction is accepted, the measurement unit 345 measures the subject using the image (the second image) in which the rolling distortion determination unit 342 determines that the rolling distortion is less than or equal to the predetermined amount. Thereby, it is possible to perform the measurement process using an image with small rolling distortion. In other words, it is possible to avoid deterioration of the measurement accuracy. In the measurement process, after the process of the measurement unit 345 is performed, the recording unit 344 adds a measurement result to the second image and records the second image in the memory 35. Recording of the image in the memory 35 in step S121 may be performed at the beginning of step S121 and the measurement result may be finally added to the memory 35. The processing in step S121 may be performed only when it is determined that there is no rolling distortion in step S110. After step S121, the processing in step S105 is performed.

With respect to points other than the above, the processes shown in FIGS. 13 and 14 are similar to processes shown in FIGS. 9 and 10.

As described above, the endoscope apparatus 1 acquires the first image and the second image. The first image is obtained by the operation in the SG exposure mode that is the first mode. The first image is generated using the pixel signals read from the pixels 54 in the simultaneous exposure lines that are simultaneously exposed. There is no rolling distortion in the image of the simultaneous exposure lines. The second image is acquired by the operation in the line exposure mode that is the second mode. The rolling distortion determination unit 342 determines a situation of occurrence of rolling distortion by comparing data of the simultaneous exposure lines in the first image with data of rows corresponding to the simultaneous exposure lines of the first image in the second image. The processing on the second image is switched in accordance with the situation of the occurrence of the rolling distortion determined by the rolling distortion determination unit 342 and a role assigned for the second image. The role assigned for the second image is one of recording and measurement.

As described above, the endoscope apparatus 1 includes the recording unit 344 and the measurement unit 345 that are processing units configured to perform a process using an image using pixel signals read by the second scan. The recording unit 344 and the measurement unit 345 perform a process using the image whose rolling distortion is determined to be less than or equal to the predetermined amount by the rolling distortion determination unit 342.

The endoscope apparatus according to each aspect of the present invention may not have a configuration other than the light source 32, the light source control unit 33, the observation optical system 60, the imaging device 21, the imaging device control unit 30, the rolling distortion determination unit 342, and the mode setting unit 343.

The image acquired in step S107 shown in FIGS. 10 and 14 is an image of frame i of FIG. 8. An operation of frame i+1, frame i+2, frame i+3, and frame i+4 as one unit may be iterated. An operation in frame i+4 is the same as an operation in frame i. In this case, the image acquired in step S107 is an image of frame i+4.

Images may be acquired in both frame i and frame i+4. In other words, after the line exposure mode is set in the light source control unit 33 and the imaging device control unit 30, the mode setting unit 343 sets the SG exposure mode in the light source control unit 33 and the imaging device control unit 30. After the SG exposure mode is set, the mode setting unit 343 sets the line exposure mode again in the light source control unit 33 and the imaging device control unit 30. The rolling distortion determination unit 342 may determine the rolling distortion in the images of frame i and frame i+4. In this case, the operation is iterated using frame i, frame i+1, frame i+2, frame i+3, and frame i+4 as one unit. Either one of the images of frame i and frame i+4 is used for recording or measurement. As the number of images used for determining the rolling distortion increases, a probability that the rolling distortion is determined to be greater than the predetermined amount in step S111 can be reduced. As a result, it is possible to minimize a frequency at which a user's operation is required in the processing in step S115 and it is possible to improve usability.

The process shown in FIGS. 9 and 10 may be changed as follows. The user performs a freeze operation by operating the operation unit 4 at a timing at which an image is desired to be recorded. The user can input a freeze instruction to the endoscope apparatus 1 by the freeze operation. In step S104, the control unit 340 determines whether or not the freeze operation has been performed on the basis of a signal from the operation unit 4.

Before the processing in step S112 is performed, the display unit 5 performs a freeze display process on the image of the subject. Specifically, the display processing unit 341 issues the freeze instruction to the image processing unit 31. The image processing unit 31 outputs a video signal corresponding to the image acquired in step S107 to the display unit 5 and freezes the image. In other words, the image processing unit 31 continues to output the same video signal to the display unit 5. The display unit 5 performs a freeze display process on the image of the subject on the basis of the video signal output from the image processing unit 31. After the user checks image quality of the image subjected to the freeze display process, the processing in step S112 is performed.

When the rolling distortion determined in step S110 is less than or equal to the predetermined amount (step S111), the image is frozen and displayed. In other words, when there is no rolling distortion or when the rolling distortion is small, the image is frozen and displayed. Therefore, after the freeze instruction is accepted, the display unit 5 performs a freeze display process on the image (the second image) for which the rolling distortion determination unit 342 determines that the rolling distortion is less than or equal to the predetermined amount. When an image recording instruction is accepted after the image is frozen and displayed, the recording unit 344 records the image (the second image) for which the rolling distortion determination unit 342 determines that the rolling distortion is less than or equal to the predetermined amount in the memory 35. Thereby, it is possible to record an image for which the user has checked that the rolling distortion is small.

A freeze display process may be performed in the process shown in FIGS. 13 and 14. For example, before the processing in step S121 is performed, the display unit 5 performs a freeze display process on the image of the subject in a process similar to that described above. After the user checks image quality of the image subjected to the freeze display process, the processing in step S121 is performed. In other words, when a measurement instruction is accepted after the image is frozen and displayed, the measurement unit 345 measures the subject using the image (the second image) for which the rolling distortion determination unit 342 determines that the rolling distortion is less than or equal to the predetermined amount. Thereby, it is possible to perform a measurement process using an image for which the user has checked that the rolling distortion is small.

As described above, when a processing instruction (an image recording instruction or a measurement instruction) is accepted after the image is frozen and displayed, the recording unit 344 and the measurement unit 345 perform a process using an image for which the rolling distortion determination unit 342 determines that the rolling distortion is less than or equal to the predetermined amount.

In the first embodiment, because high-speed reading driving is unnecessary, heat generation of the imaging device can be suppressed. Also, because the rolling distortion determination unit 342 determines the situation of the occurrence of the rolling distortion, it is possible to acquire an image with small rolling distortion.

In the SG exposure mode, an image including pixel signals of simultaneous exposure lines is acquired. Because all the pixels 54 in the simultaneous exposure lines are exposed simultaneously, rolling distortion does not occur. Using this image, the rolling distortion determination unit 342 can reliably determine the situation of the occurrence of the rolling distortion.

When half of all the rows in the array of the plurality of pixels 54 are simultaneous exposure lines, a period from time t24 to time t26 and a period from time t26 to time t27 shown in FIG. 8 are halves of the frame cycle. In this case, a relatively long period is secured as the exposure period of the pixels 54 in the simultaneous exposure lines. To allow observation within a narrower space using the endoscope apparatus 1, it is preferable that the insertion unit 2 be made thinner. When a diameter of the insertion unit 2 is reduced and the illumination optical system 61 of the optical adapter 6 becomes small, an intensity of illumination light tends to be insufficient. In the first embodiment, because the available SG exposure period can be made relatively long, an exposure amount of the pixels 54 in the simultaneous exposure lines can be increased. Thereby, because a signal to noise (S/N) ratio of the image is improved, the detection accuracy of the rolling distortion also increases in the endoscope apparatus 1 in which the diameter of the insertion unit 2 is reduced.

Second Embodiment

Figure 15:
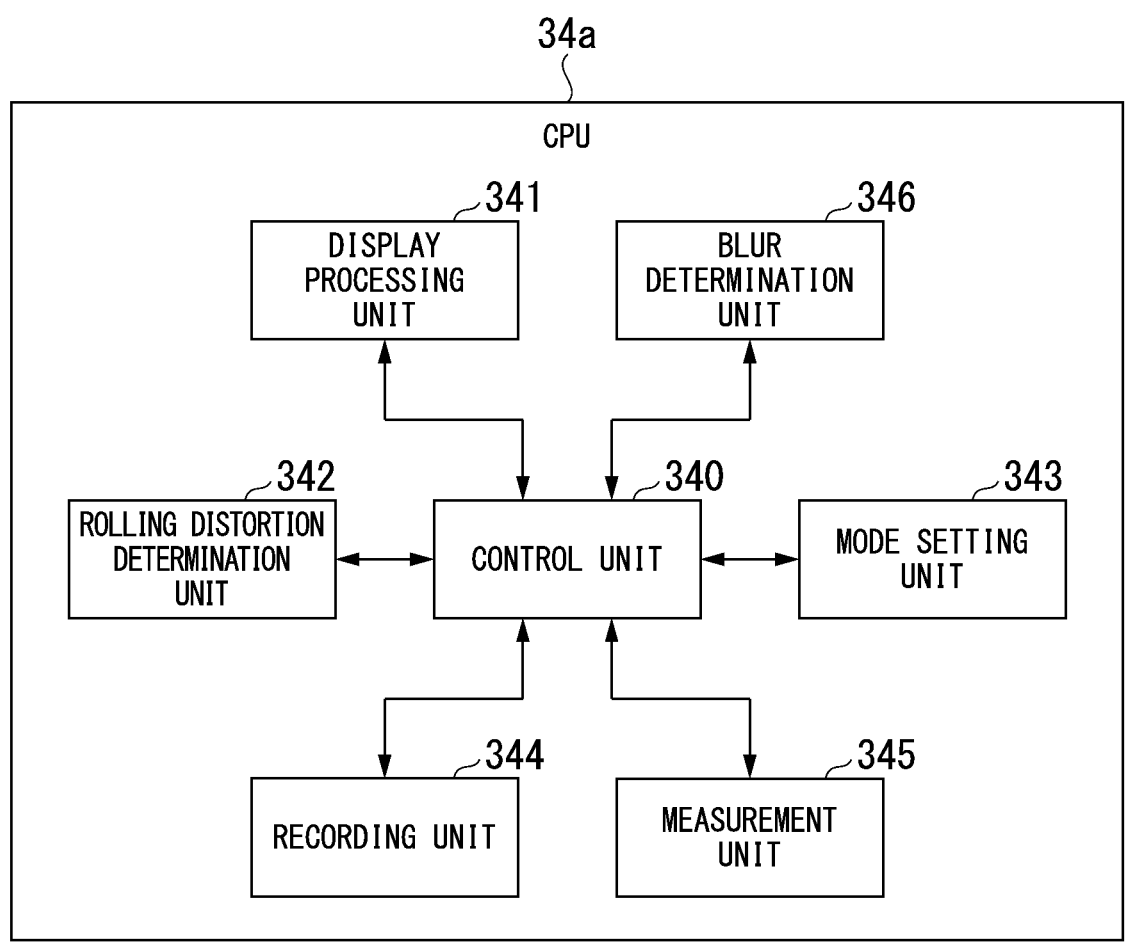
FIG. 15 is a block diagram showing a functional configuration of a CPU according to a second embodiment of the present invention.

In the endoscope apparatus 1 according to the second embodiment of the present invention, the CPU 34 in the first embodiment is changed to a CPU 34a shown in FIG. 15. FIG. 15 shows a functional configuration of the CPU 34a. Differences from the configuration shown in FIG. 3 will be described in the configuration shown in FIG. 15.

In addition to the configuration shown in FIG. 3, the CPU 34a has a blur determination unit 346. The blur determination unit 346 determines the occurrence of a blur (a motion blur) in a first image and a second image by comparing images of a plurality of frames. The images on which the determination is made by the blur determination unit 346 are images of two frames. The images on which the determination of the blur determination unit 346 is made are images of two frames acquired by an operation in the line exposure mode (second images) or images of two frames acquired by the operation in the SG exposure mode (first images). These images are generated using the pixel signals read from the pixels 54 in the simultaneous exposure lines that are simultaneously exposed.

Specifically, when an instruction of any one of freezing, image recording, and measurement is accepted, the blur determination unit 346 determines the occurrence of a blur in the second image. When the blur determination unit 346 determines that the blur in the second image is less than or equal to the predetermined amount, the mode setting unit 343 sets the SG exposure mode in the light source control unit 33 and the imaging device control unit 30. When the blur determination unit 346 determines that the blur in the first image is less than or equal to the predetermined amount, the mode setting unit 343 sets the line exposure mode in the light source control unit 33 and the imaging device control unit 30.

With respect to points other than the above, the configuration shown in FIG. 15 is similar to the configuration shown in FIG. 3.

Figure 16:
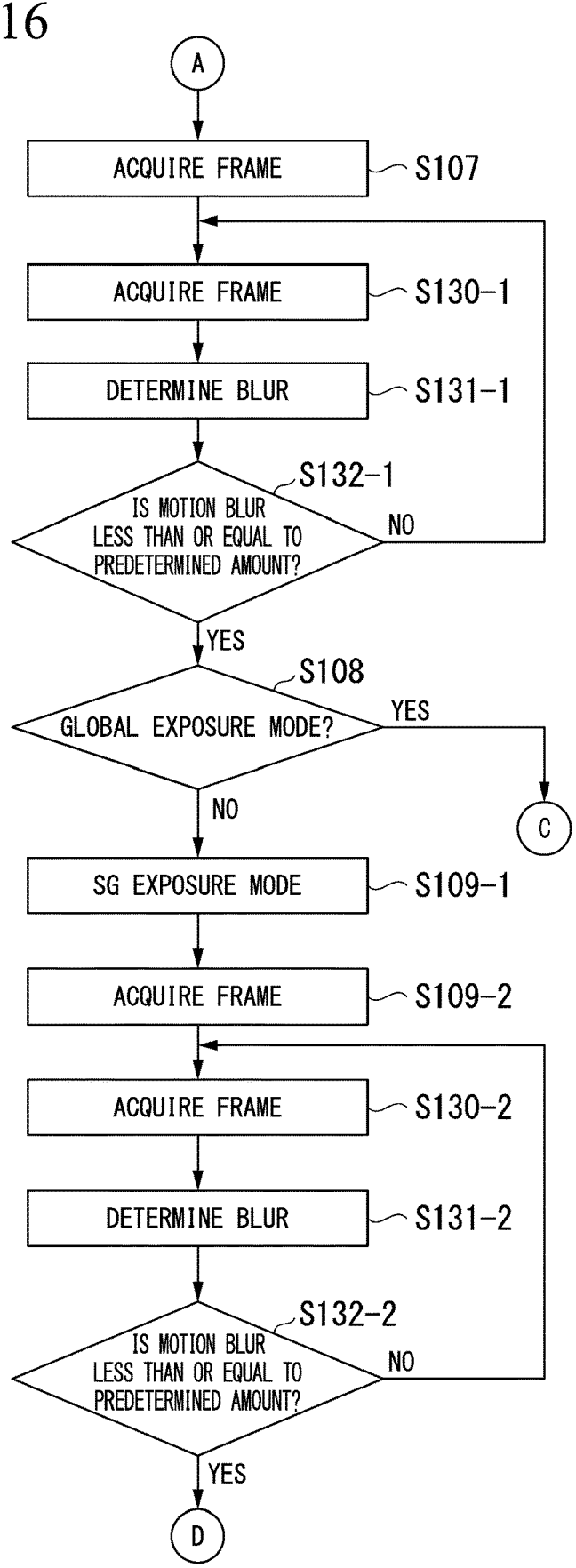
FIG. 16 is a flowchart showing an operation of an endoscope apparatus according to the second embodiment of the present invention.
Figure 17:
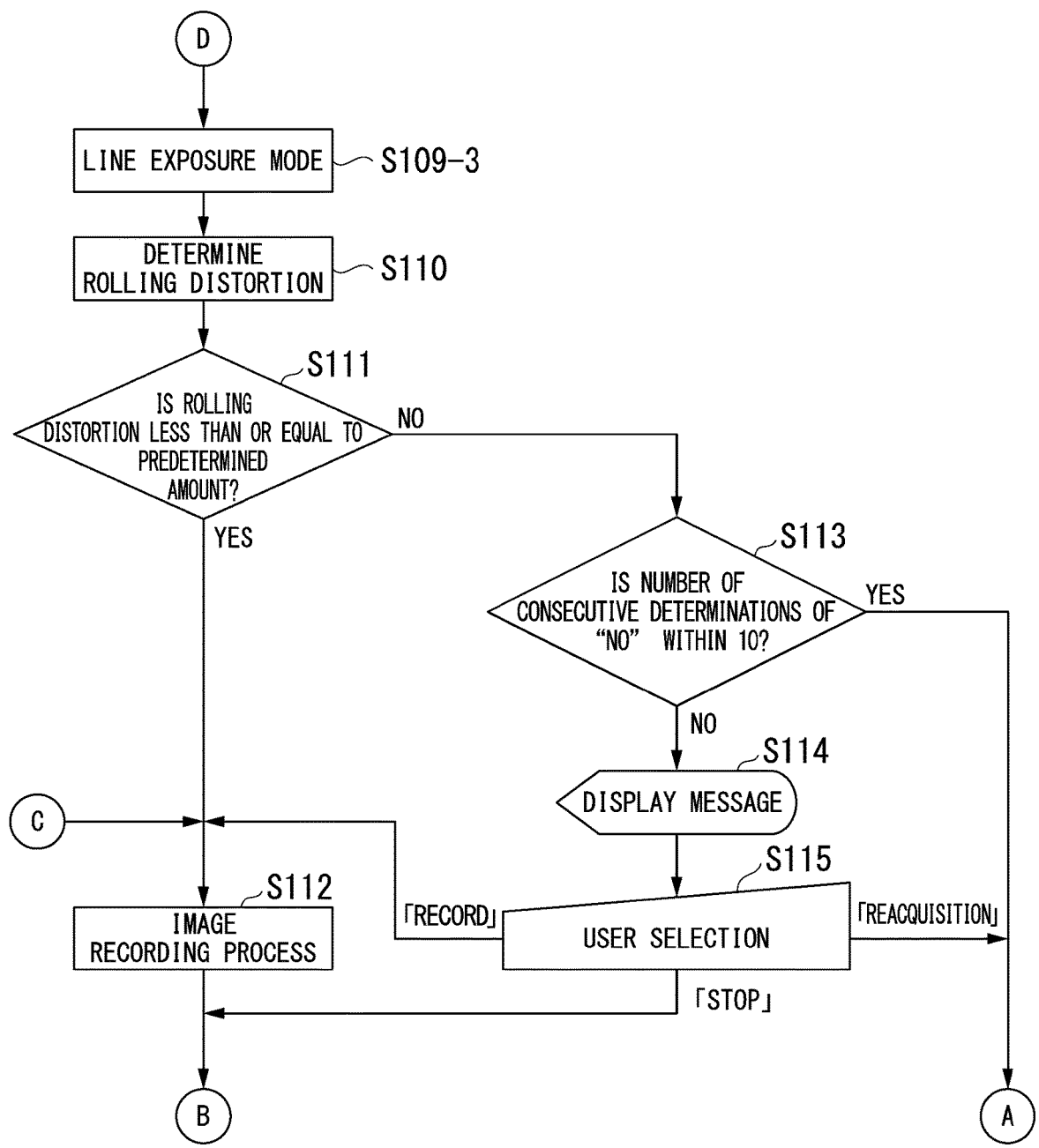
FIG. 17 is a flowchart showing an operation of the endoscope apparatus according to the second embodiment of the present invention.

The operations shown in FIGS. 9 and 10 in the first embodiment are changed to operations shown in FIGS. 9, 16, and 17. The operation shown in FIG. 9 is common to the first and second embodiments. The operation shown in FIG. 10 in the first embodiment is changed to operations shown in FIGS. 16 and 17. The operation of the endoscope apparatus 1 will be described with reference to FIGS. 16 and 17. Differences from the operation shown in FIG. 10 will be described in the operations shown in FIGS. 16 and 17.

When the control unit 340 determines that an image recording operation has been performed in step S104, the processing in step S107 is performed. After step S107, processing similar to that of step S107 is performed again (step S130-1). In the processing in steps S107 and S130-1, images of two frames are acquired in the global exposure mode or the line exposure mode.

After step S130-1, the blur determination unit 346 determines the situation of occurrence of a motion blur by comparing the images of the two frames acquired by the operation in the global exposure mode or the line exposure mode (step S131-1). When the motion blur determined in step S131-1 is greater than the predetermined amount (step S132-1), the processing in step S130-1 is performed. Thereafter, the determination in step S131-1 is made again. In other words, when the situation in which the motion blur is greater than the predetermined amount continues, the image acquisition in step S130-1 is iterated. In this case, the imaging device 21 iteratively generates an image (a second image) using the pixel signals generated by all the pixels 54 when the light source 32 is turned on. In second and subsequent determinations in step S131-1, the image acquired in step S130-1 immediately before step S131-1 and the image acquired in step S130-1 immediately before the determination in step S131-1 is made one time ago are used. When the motion blur determined in step S131-1 is less than or equal to the predetermined amount (step S132-1), the processing in step S108 is performed. Every time the second image is acquired in step S107 and step S130-1, the acquired second image is displayed on the display unit 5.

When the mode set in the light source control unit 33 and the imaging device control unit 30 is the global exposure mode (step S108), the processing in step S112 is performed. In step S104, when the control unit 340 determines that the image recording operation has been performed and the mode set in the light source control unit 33 and the imaging device control unit 30 is not the global exposure mode (step S108), the processing in steps S109-1 and S109-2 is performed.

After step S109-2, processing similar to the processing in step S109-2 is performed again (step S130-2). In the processing in steps S109-2 and S130-2, two frames of images are acquired in the SG exposure mode. For example, the operation configured in frames i+1 to i+3 shown in FIG. 8 is performed twice.

After step S130-2, the blur determination unit 346 determines the situation of occurrence of the motion blur by comparing the images of the two frames acquired by the operation in the SG exposure mode (step S131-2). When the motion blur determined in step S131-2 is greater than the predetermined amount (step S132-2), the processing in step S130-2 is performed. Thereafter, the determination in step S131-2 is made again. In other words, if a situation in which the motion blur is greater than the predetermined amount continues, the image acquisition in step S130-2 is iterated. In this case, when the light source 32 is turned on, the imaging device 21 iteratively generates an image (a first image) using pixel signals generated by the pixels 54 in all the simultaneous exposure lines. In the second and subsequent determinations in step S131-2, the image acquired in step S130-2 immediately before step S131-2 and the image acquired in step S130-2 immediately before the determination in step S131-2 is made one time ago are used. The first image acquired in step S109-2 and step S130-2 is not displayed on the display unit 5.

When the motion blur determined in step S131-2 is less than or equal to the predetermined amount (step S132-2), the processing in step S109-3 and the processing in step S110 are performed. The processing in steps 109-3 and S110 may be performed only when there is no motion blur.

With respect to points other than the above, the operations shown in FIGS. 16 and 17 are similar to those shown in FIG. 10.

Step S104 shown in FIG. 9 may be changed to step S120 shown in FIG. 13 and step S112 shown in FIG. 17 may be changed to step S121 shown in FIG. 14.

In the second embodiment, an image without camera shake and a subject blur as well as rolling distortion is used for determining rolling distortion. Thus, the accuracy of the rolling distortion determination is improved. As a result, it is possible to implement recording of images of higher image quality and more accurate measurement.

Also, the processing in steps S130-1 and S130-2 may be eliminated and the blur determination unit 346 may analyze the image of one frame to determine the occurrence of a blur.

Also, the process may proceed to step S108 immediately after step S107. Specifically, when an instruction of any one of freezing, image recording, and measurement is accepted, the mode setting unit 343 sets the SG exposure mode (the first mode) in the light source control unit 33 and the imaging device control unit 30. When the blur determination unit 346 determines that the blur in the first image is less than or equal to the predetermined amount, the mode setting unit 343 sets the line exposure mode (the second mode) in the light source control unit 33 and the imaging device control unit 30. Alternatively, the processing between step S107 and step S108 is not changed and the process may proceed to step S109-3 immediately after step S109-2. According to a configuration thereof, it is possible to shorten a time until the presence or absence of rolling distortion is known from the measurement operation performed by the user.

Third Embodiment

A third embodiment of the present invention will be described using the endoscope apparatus 1 shown in FIGS. 1 and 2. In the third embodiment, when a temperature measured by the temperature sensor 23 is less than or equal to a first threshold value and greater than a second threshold value, images are sequentially acquired in a line exposure mode and an SG exposure mode. For example, the first threshold value is 80° C. and the second threshold value is 60° C. The display unit 5 displays an image acquired in the line exposure mode. The rolling distortion determination unit 342 determines rolling distortion using the image acquired in the line exposure mode and the image acquired in the SG exposure mode. When the rolling distortion determination unit 342 determines that rolling distortion greater than the predetermined amount has occurred, the display unit 5 displays a warning.

Figure 18:
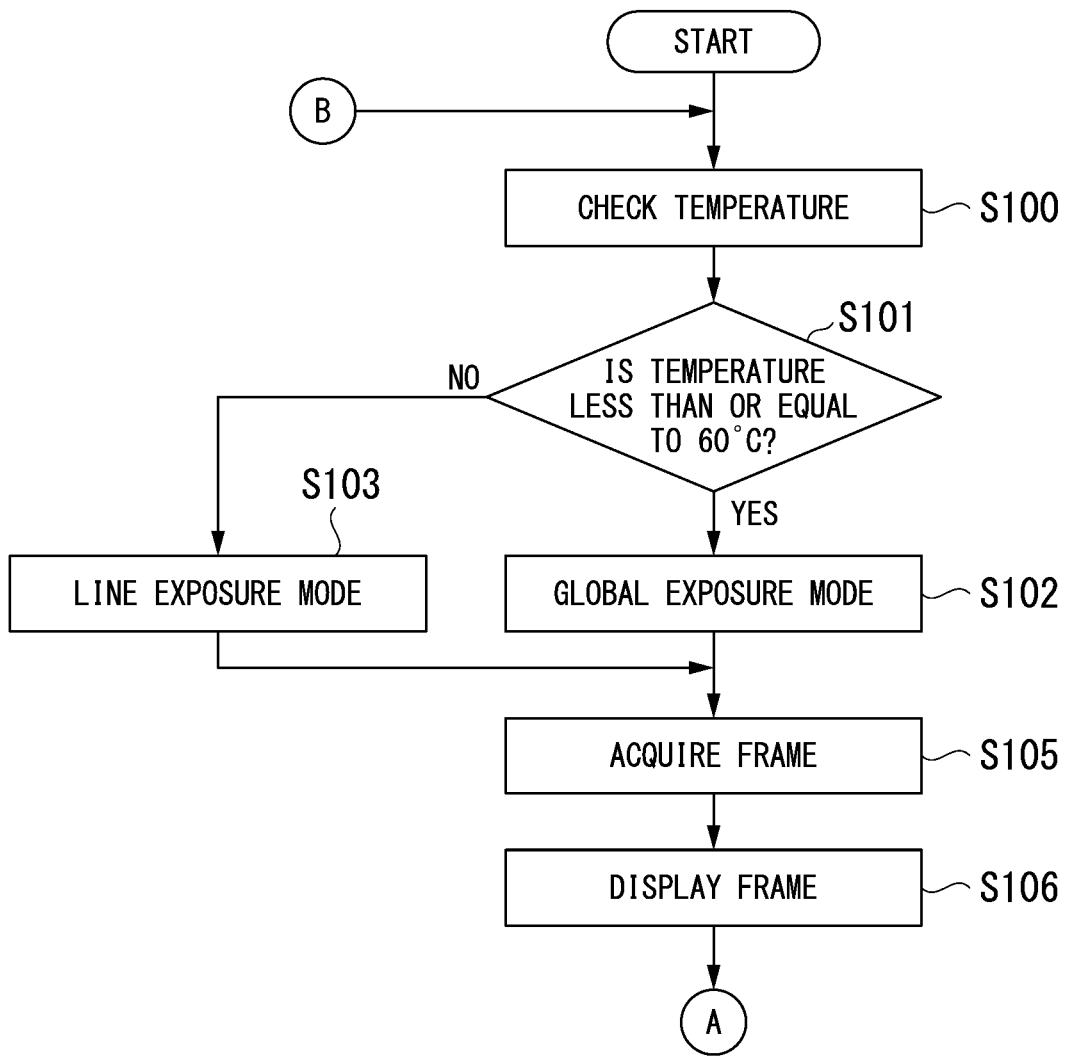
FIG. 18 is a flowchart showing an operation of an endoscope apparatus according to a third embodiment of the present invention.
Figure 19:
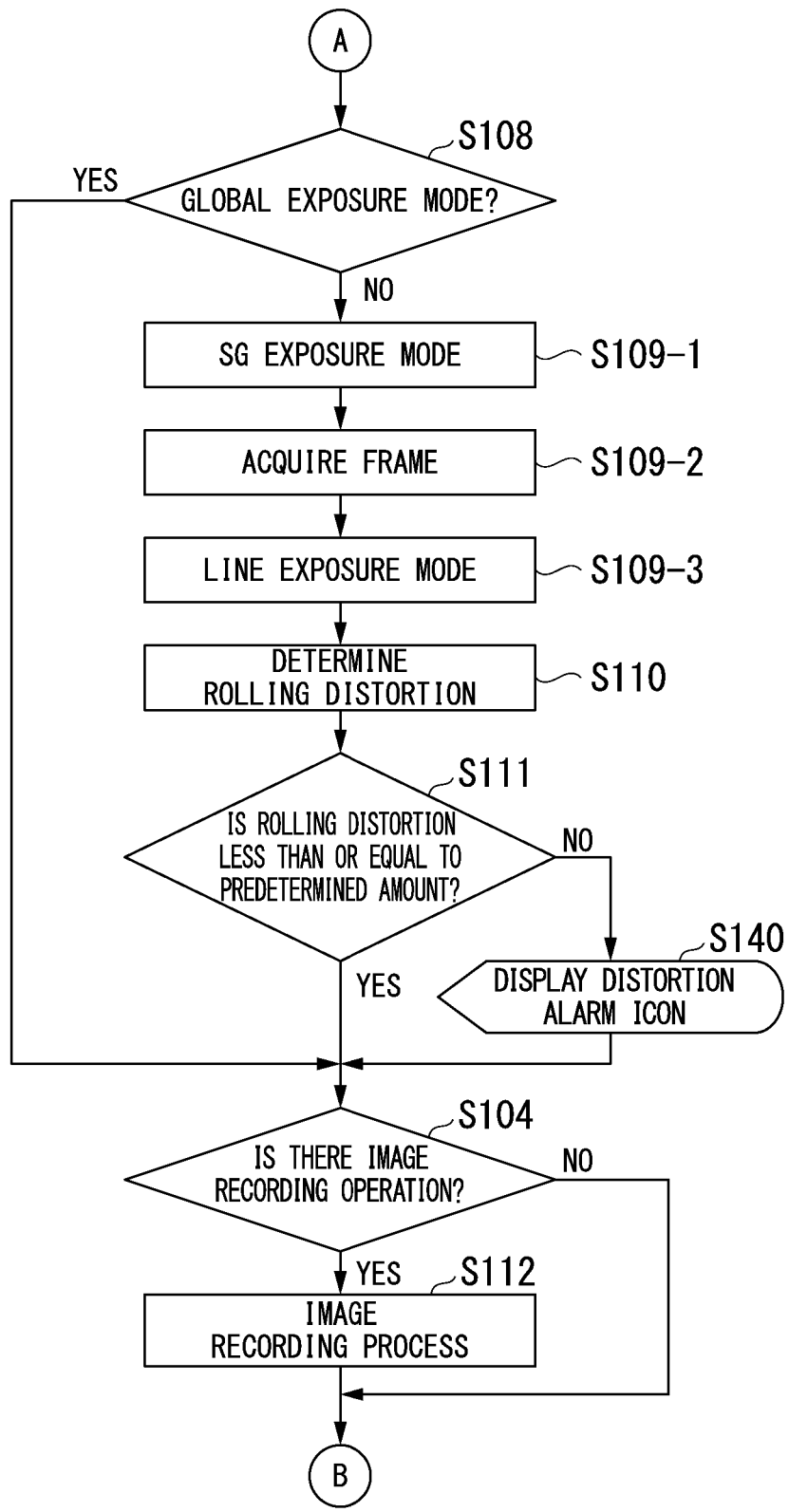
FIG. 19 is a flowchart showing an operation of the endoscope apparatus according to the third embodiment of the present invention.

The operations shown in FIGS. 9 and 10 in the first embodiment are changed to operations shown in FIGS. 18 and 19. An operation of the endoscope apparatus 1 will be described with reference to FIGS. 18 and 19. In the operations shown in FIGS. 18 and 19, differences from the operations shown in FIGS. 9 and 10 will be described.

After step S102 or step S103, the processing in step S105 is performed. As described above, when the global exposure mode is set, pixel signals of one frame are acquired by the operation shown in FIG. 7 in step S105. When the line exposure mode is set, pixel signals of one frame are acquired by the operation shown in FIG. 6 in step S105. After step S105, the processing in step S106 is performed. After step S106, the processing in step S104 is performed in accordance with the set mode (step S108). Alternatively, the processing in steps S109-1, S109-2, and S109-3 is performed.

When the rolling distortion determined in step S110 is greater than a predetermined amount (step S111), the display processing unit 341 generates graphic data for displaying a distortion warning icon. The graphic data generated by the display processing unit 341 is output to the image processing unit 31. The image processing unit 31 generates a video signal for display by synthesizing image data on which image processing has been performed with the graphic data. The display unit 5 displays the distortion warning icon on the basis of the video signal output from the image processing unit 31 (step S140). As a result, the display unit 5 displays a warning.

Figure 20:
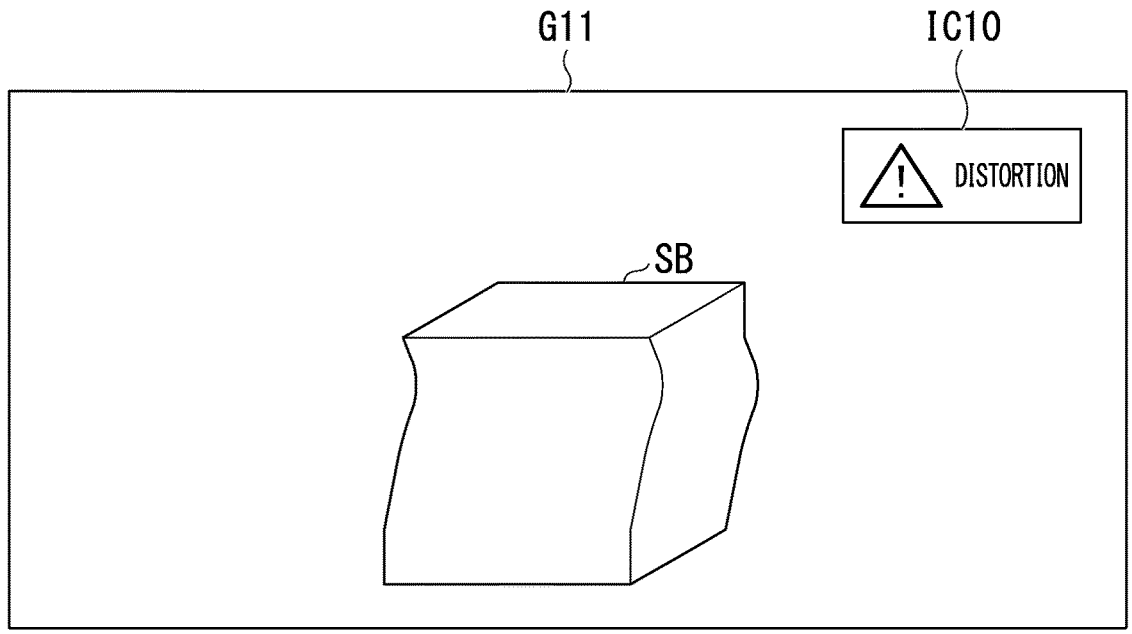
FIG. 20 is a reference diagram showing an image displayed on a display unit in the third embodiment of the present invention.

FIG. 20 shows an image G11 displayed by the display unit 5 in step S140. Rolling distortion occurs in a subject SB of the image G11. The image G11 includes a distortion warning icon IC10. The distortion warning icon IC10 is a mark for notifying the user of the occurrence of rolling distortion greater than a predetermined amount. By displaying the distortion warning icon IC10, the user can know that rolling distortion greater than the predetermined amount has occurred.

When the mode set in the light source control unit 33 and the imaging device control unit 30 is the global exposure mode (step S108), the processing in step S104 is performed. When the rolling distortion determined in step S110 is less than or equal to the predetermined amount (step S111), the processing in step S104 is performed. After the processing in step S140 is performed, the processing in step S104 is performed.

If the control unit 340 determines that the image recording operation has not been performed in step S104, the processing in step S100 is performed. If the control unit 340 determines that the image recording operation has been performed in step S104, the processing in step S112 is performed. In this case, the recording unit 344 records the image acquired in step S105 in the memory 35. After the processing in step S112 is performed, the processing in step S100 is performed.

With respect to points other than those described above, operations shown in FIGS. 18 and 19 are similar to the operations shown in FIGS. 9 and 10.

Step S104 shown in FIG. 19 may be changed to step S120 shown in FIG. 13 and step S112 shown in FIG. 19 may be changed to step S121 shown in FIG. 14.

As described above, when a processing instruction (an image recording instruction or a measurement instruction) is accepted after the warning is displayed by the display unit 5, the recording unit 344 and the measurement unit 345 perform processes indicated in the instructions using an image acquired by the processing in step S105 without depending on the rolling distortion determination unit 342.

When an image recording operation or a measurement operation is performed in a state in which the distortion warning icon is displayed, a process for attracting attention of the user may be performed. Thereafter, when an image without rolling distortion can be acquired by an operation of the line exposure mode, image recording or measurement may be performed. In other words, when a processing instruction is accepted after the warning is displayed on the display unit 5, the recording unit 344 and the measurement unit 345 may perform processes using an image for which the rolling distortion determination unit 342 determine that the rolling distortion is less than or equal to the predetermined amount and which is acquired by the processing in step S105.

Figure 21:
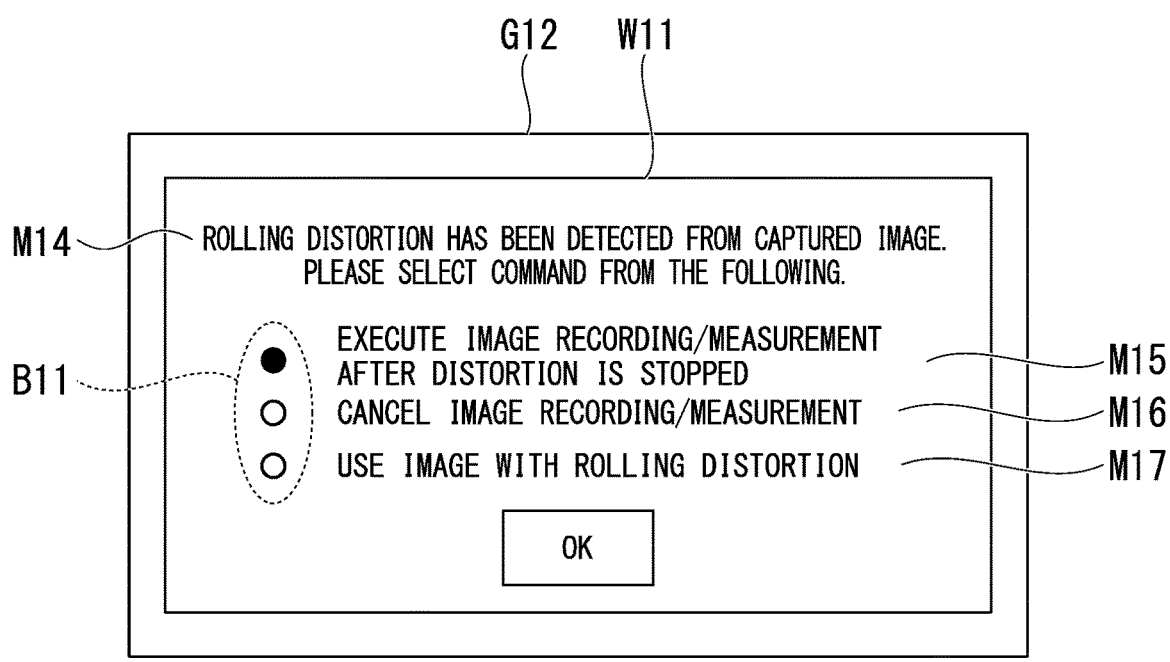
FIG. 21 is a reference diagram showing an image displayed on the display unit in the third embodiment of the present invention.

FIG. 21 shows an image G12 displayed by the display unit 5 for attracting attention of the user. The image G12 includes a window W11. The window W11 includes a message M14 indicating the situation of the occurrence of the rolling distortion. Further, the window W11 includes a message M15, a message M16, and a message M17 for allowing the user to select a countermeasure. The message M15 indicates the execution of an image recording process or a measurement process after the rolling distortion is stopped. The message M16 indicates the stopping of the image recording process or the measurement process. The message M17 indicates the use of an image in which rolling distortion has occurred. Further, the window W11 includes a check box B11 provided in correspondence with each message. By operating the operation unit 4, the user inputs a selection result to the check box B11. When the method corresponding to the message M15 is selected, the image acquisition in the line exposure mode and the SG exposure mode and the determination of the rolling distortion are iterated until the rolling distortion is less than or equal to the predetermined amount.

In the third embodiment, when the distortion warning icon is displayed, the user avoids the image recording operation or the measuring operation, so that it is possible to reduce a possibility that an image in which the rolling distortion greater than the predetermined amount has occurred will be used.

Fourth Embodiment

A fourth embodiment of the present invention will be described using the endoscope apparatus 1 shown in FIGS. 1 and 2. In the first embodiment, the pixels 54 of the odd-numbered lines are set in simultaneous exposure lines so that the rolling distortion can be detected in all of the imaging region. In the fourth embodiment, when a region of interest is preset, rows included in the region of interest are set as simultaneous exposure lines. Thereby, the rolling distortion determination unit 342 can determine rolling distortion in accordance with a position of the region of interest. The number of rows set as simultaneous exposure lines is determined in accordance with a time required for exposure of the pixels 54 in the region of interest. For example, if an exposure time of one-third of the frame cycle is required, an upper limit of the number of rows set as the simultaneous exposure lines is two-thirds of the total number of rows.

Figure 22:
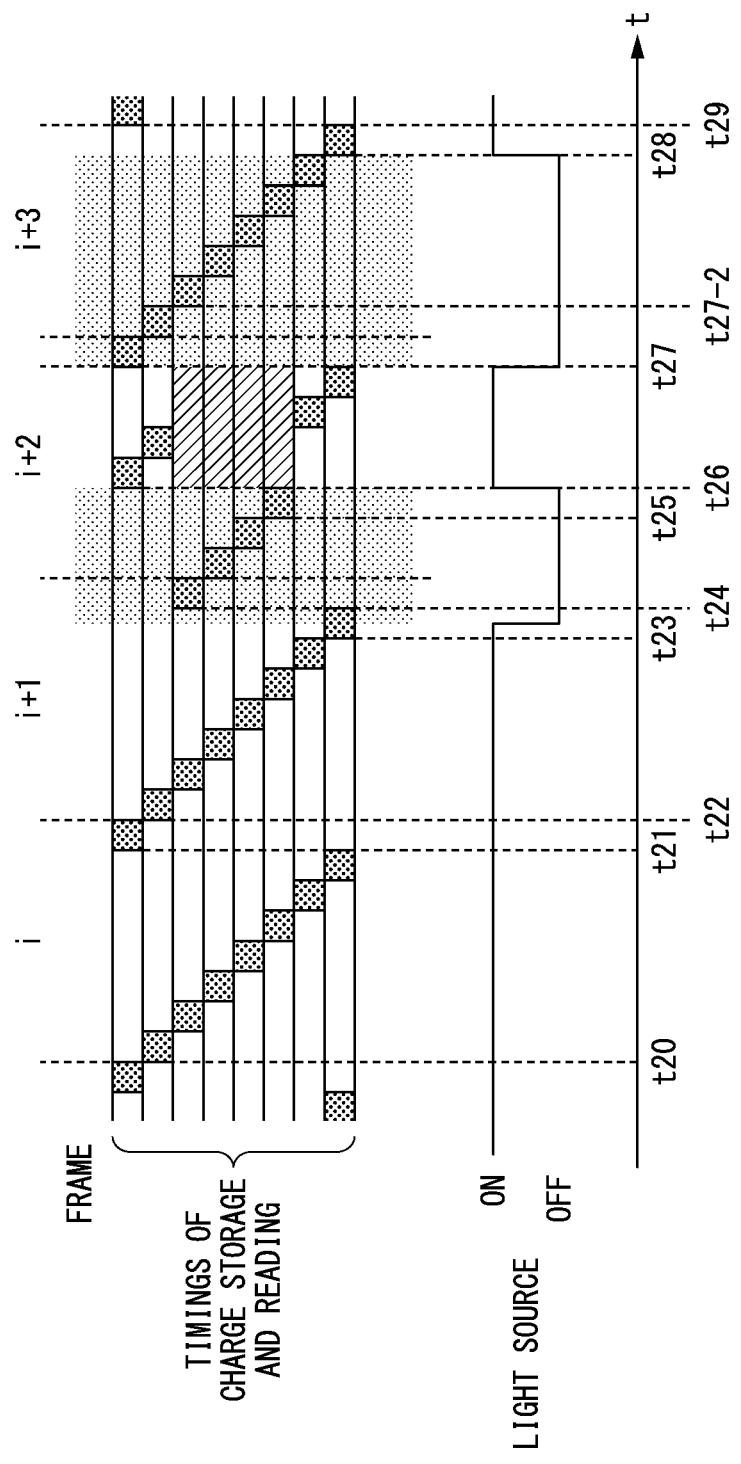
FIG. 22 is a timing chart showing operations of an imaging device and a light source in a fourth embodiment of the present invention.

FIG. 22 shows operations of the imaging device 21 and the light source 32 in a mode in which line exposure and SG exposure are combined. In the upper-side drawing of FIG. 22, a horizontal direction indicates time and a vertical direction indicates a position of a row of the pixels 54 of the imaging device 21. In FIG. 22, the operations in the pixels 54 of eight rows are shown. A top row is a first row and a bottom row is an eighth row. In the lower-side drawing of FIG. 22, a lateral direction indicates time and a longitudinal direction indicates a state of the light source 32. "ON" indicates a state in which the light source 32 is turned on. "OFF" indicates a state in which the light source 32 is turned off.

In FIG. 22, timings of charge storage and reading of each row in the array of a plurality of pixels 54 are shown. Most of the operation shown in FIG. 22 is similar to the operation shown in FIG. 8. The operation shown in FIG. 22 will be described with respect to differences from the operation shown in FIG. 8. The control of the imaging device 21 during a period from time t24 to time t27 is different from the operation shown in FIG. 8.

In FIG. 22, the simultaneous exposure lines include two or more consecutive rows. Specifically, the region of interest is set as a part of the imaging region and a plurality of rows including the region of interest become simultaneous exposure lines. FIG. 22 shows a case in which the region of interest is set at the center of the imaging region. In FIG. 22, simultaneous exposure lines cover a quarter of the number of all rows upward and downward from the center of the imaging area. In other words, the simultaneous exposure lines are third to sixth rows.

At time t24, reading of pixel signals of the pixels 54 of the third row is started. At time t24, reading of pixel signals of frame i+1 of the pixels 54 of the simultaneous exposure lines is started. Thereafter, the pixel signals of frame i+1 of the pixels 54 of the simultaneous exposure lines are sequentially read for each row. At time t25, reading of the pixel signals of the pixels 54 of the sixth row is started. At time t26 when a predetermined time has elapsed from time t25, the reading of the pixel signals of frame i+1 of the pixels 54 of the simultaneous exposure lines is completed. During a period from time t26 to time t27, pixel signals of the pixels 54 of the first row, the second row, the seventh row, and the eighth row, which are non-simultaneous exposure lines, are read.

Regarding other points, the operation shown in FIG. 22 is similar to the operation shown in FIG. 8. Also, a timing at which the light source 32 is switched from turning-on to turning-off may be delayed until time t27-2 at which reading of the pixel signals of frame i+2 of the pixels 54 of the third row that is a first simultaneous exposure line is started. In this case, an available SG exposure period can be made longer.

The region of interest may be automatically set so that a region of strong texture and a region of intermediate gradation are included in the region of interest at the maximum in the image previously acquired in the line exposure mode. Also, as long as the number of rows set as simultaneous exposure lines does not exceed the upper limit, the region of interest may be divided into a plurality of regions.

In the fourth embodiment, the region of interest includes two or more consecutive rows. In the region of interest, the detection accuracy of the motion vector increases particularly in the direction orthogonal to the row, i.e., the vertical direction. Thus, it is possible to detect rolling distortion less than the rolling distortion detected in the first embodiment.

Fifth Embodiment

A fifth embodiment of the present invention will be described using the endoscope apparatus 1 shown in FIGS. 1 and 2. The imaging device 21 in the fifth embodiment has a global reset function. The imaging device 21 simultaneously resets charges of all the pixels 54 by the global reset function and resumes charge storage in all the pixels 54. Thereby, exposure start times in all the pixels 54 are the same.

The operations shown in FIGS. 6 and 7 in the first embodiment are similar to an operation in the fifth embodiment. The operation shown in FIG. 8 in the first embodiment is changed to an operation shown in FIG. 23.

Figure 23:
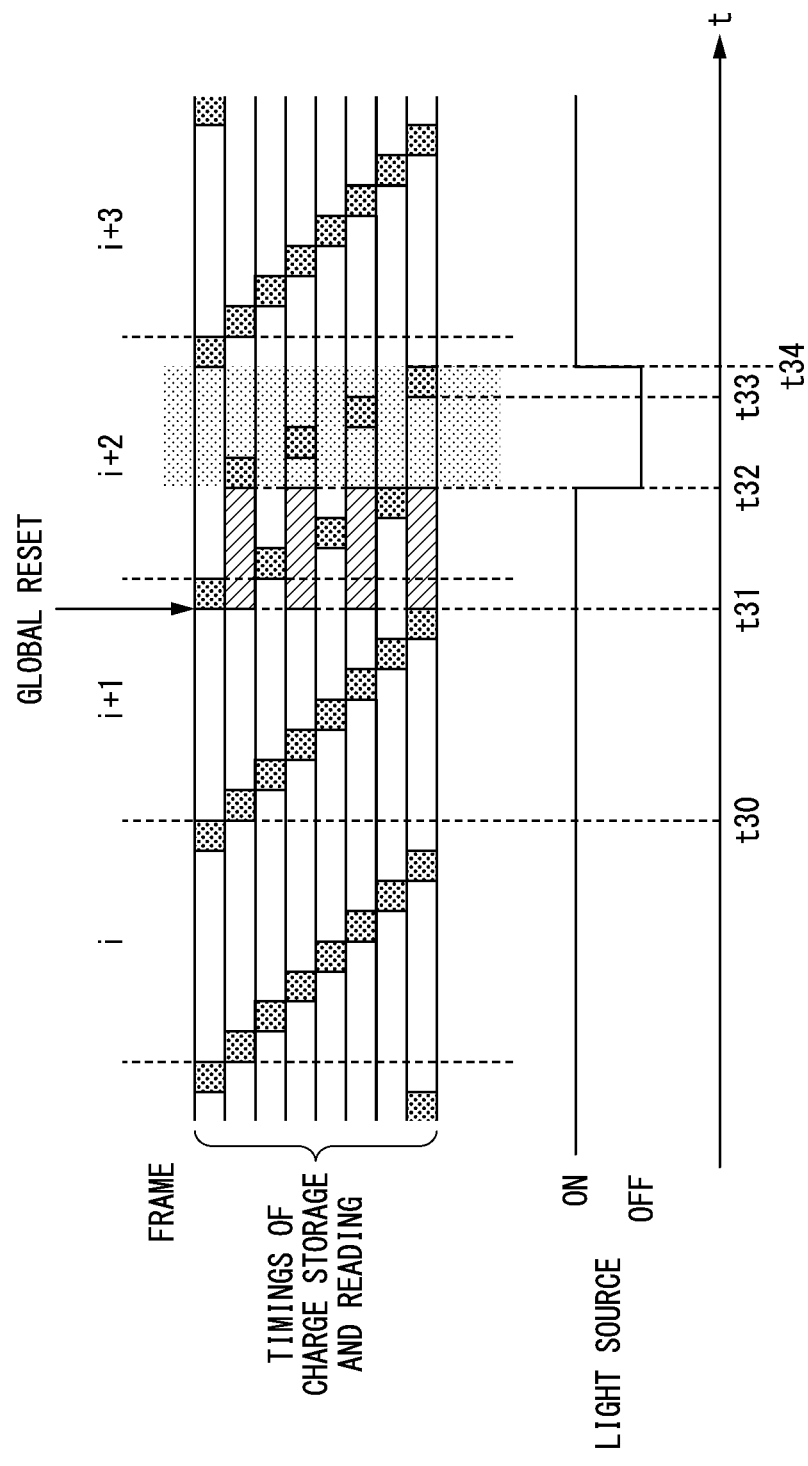
FIG. 23 is a timing chart showing operations of an imaging device and a light source in a fifth embodiment of the present invention.

FIG. 23 shows operations of an imaging device 21 and a light source 32 in a mode in which line exposure and SG exposure are combined. In the upper-side drawing of FIG. 23, a horizontal direction indicates time and a vertical direction indicates a position of a row of the pixels 54 of the imaging device 21. In FIG. 23, the operations in the pixels 54 of eight rows are shown. A top row is a first row and a bottom row is an eighth row. In the lower-side drawing of FIG. 23, a lateral direction indicates time and a longitudinal direction indicates a state of the light source 32. "ON" indicates a state in which the light source 32 is turned on. "OFF" indicates a state in which the light source 32 is turned off.

In FIG. 23, timings of charge storage and reading of each row in an array of a plurality of pixels 54 are shown. An operation shown in FIG. 23 includes an operation of three frames. Frame i is a frame to be subjected to line exposure and frame i+1 is a frame subjected to SG exposure. An operation in frame i+3 is the same as an operation in frame i. The operation in frame i+4 following frame i+3 is the same as the operation in frame i+1.

In FIG. 23, a frame cycle based on a timing at which reading of pixel information of a previous frame is completed in pixels 54 of a first row, i.e., a start timing of an available storage period, is shown. In frame i, an operation in a line exposure mode that is a second mode is performed. The operation in frame i is similar to the operation shown in FIG. 8.

The operations in frame i+1 and frame i+2 will be described. In frame i+1 and frame i+2, the operation in the SG exposure mode that is a first mode is performed. In the operation shown in FIG. 23, a mode setting unit 343 sets the line exposure mode in a light source control unit 33 and an imaging device control unit 30, and then sets the SG exposure mode in the light source control unit 33 and the imaging device control unit 30.

In frame i+1, the available storage periods of the pixels 54 in each row are sequentially started in an arrangement order of rows from time t30 to time t31. This operation is similar to an operation during a period from time t22 to time t24 shown in FIG. 8.

When pixel signals generated by the pixels 54 in frame i+1 are read, the order of rows in which the pixel signals are read is different from an order in the line exposure mode. In other words, the order of rows scanned by the imaging device 21 is different from the order in the line exposure mode. Specifically, pixel signals of the pixels 54 of odd-numbered rows are first read. After reading of the pixel signals of the pixels 54 of the odd-numbered rows are completed, pixel signals of the pixels 54 of even-numbered rows are read.

In the fifth embodiment, simultaneous exposure lines are the even-numbered rows. In frame i+1, pixels 54 of two or more rows that are the simultaneous exposure lines are simultaneously exposed. In other words, in frame i+1, exposure periods of the pixels 54 of two or more rows which are simultaneous exposure lines are the same. The odd-numbered rows other than the simultaneous exposure lines are non-simultaneous exposure lines.

When the SG exposure mode is set, the imaging device control unit 30 causes the imaging device 21 to simultaneously reset the pixels 54 in all the simultaneous exposure lines. At time t31 at which reading of the pixel signals of frame i of all the pixels 54 is completed, the imaging device control unit 30 causes the pixels 54 of all the rows including the simultaneous exposure lines to be simultaneously reset. Thereby, all the pixels 54 are simultaneously reset. In other words, a global reset process is performed. Although the pixels 54 of all the rows are reset in FIG. 23, only the pixels 54 of all the simultaneous exposure lines may be reset. Also, a reset timing may be any timing within a period from time t31 to time t32.

The available storage periods of the pixels 54 in all the simultaneous exposure lines are simultaneously started by the global reset process. By intermittently turning the light source 32 off after the pixels 54 in all the simultaneous exposure lines are reset, the exposure periods of the pixels 54 in the simultaneous exposure lines can be made the same. In other words, the SG exposure can be performed when the pixel signals of frame i+2 of the pixels 54 in the simultaneous exposure lines are generated. A period from time t31 to time t32 is the available SG exposure period.

When the SG exposure mode is set, the light source control unit 33 causes the light source 32 to be turned on during a period including all or a part of the available SG exposure period. Specifically, after the pixels 54 in all the simultaneous exposure lines are simultaneously reset, the light source control unit 33 causes the light source 32 to be turned on during a period including all or a part of a period during which the available storage periods of the pixels 54 in all the simultaneous exposure lines overlap. When the light source 32 is turned on, the imaging device 21 generates an image (a first image) using pixel signals generated by the pixels 54 in all the simultaneous exposure lines.

After time t31 when the global reset process is performed, reading of the pixel signals of the pixels 54 of the second row that is the simultaneous exposure line is started at time t32 as will be described below. During a period from time t31 to time t32, the available storage periods of the pixels 54 in all the simultaneous exposure lines overlap. The light source 32 is turned on during this period. In other words, in FIG. 23, the light source 32 is turned on during a period including all of a period during which the available storage periods of the pixels 54 overlap in all the simultaneous exposure lines. The light source 32 may be turned on in only a part of the period from time t31 to time t32. During the period from time t31 to time t32, the pixels 54 in all the simultaneous exposure lines are simultaneously exposed. During the period from time t31 to time t32, the pixels 54 in the simultaneous exposure lines are subjected to exposure of frame i+1. In FIG. 23, before time t31, the light source control unit 33 causes the light source 32 to be maintained in the turned-on state.

At time t32, reading of pixel signals of the pixels 54 of the second row is started. Thereby, the available storage period of the pixels 54 of the second row ends and then the pixels 54 of the second row output pixel signals. At time t32, reading of the pixel signals of the pixels 54 of the simultaneous exposure lines is started. Thereafter, reading of the pixel signals of the pixels 54 of the simultaneous exposure lines is sequentially performed for each row. At time t33, reading of the pixel signals of the pixels 54 of the eighth row is started. Thereby, the available storage period of the pixels 54 of the eighth row ends and the pixels 54 of the eighth row output the pixel signals. At time t34 when a predetermined time has elapsed from time t33, the reading of the pixel signals of the pixels 54 of the simultaneous exposure lines is completed.

When the SG exposure mode is set, the imaging device control unit 30 causes the imaging device 21 to perform a first scan for reading pixel signals from the pixels 54 in the simultaneous exposure lines by consecutively scanning all the simultaneous exposure lines. Specifically, after the pixels 54 in all the simultaneous exposure lines are reset at the same time, the imaging device control unit 30 causes the imaging device 21 to perform the first scan. During the period from time t32 to time t34, pixel signals are sequentially output from the pixels 54 in the simultaneous exposure lines by the first scan.

When pixel signals constituting an image of frame i+1 are read from the pixels 54 in the simultaneous exposure lines, the light source 32 is turned off. When the SG exposure mode is set, the light source control unit 33 causes the light source 32 to be turned off during a period including all of a period during which the first scan is performed. In FIG. 23, the light source 32 is turned off during a period including times t32 to t34. At time t32, the light source control unit 33 switches the light source 32 from the turned-on state to the turned-off state. During a period from time t32 to time t34, pixel signals are read from the pixels 54 in all the simultaneous exposure lines. Thus, in FIG. 23, the light source 32 is turned off during a period including all of the period during which the first scan is performed.

The imaging device control unit 30 causes the imaging device 21 to perform the global reset process before a reference timing at which the available storage period ends in the pixel 54 in which charge storage of frame i+1 initially starts among the pixels 54 of the simultaneous exposure line. Among the pixels 54 of the simultaneous exposure lines, the pixel 54 in which the charge storage of frame i+1 initially starts is the pixel 54 of the second row. The imaging device control unit 30 determines a timing of the global reset process so that a time from the global reset timing to the reference timing becomes the exposure time that is determined to be appropriate by the image processing unit 31. The timing of the global reset process is the same as the timing at which the available storage period is started in the pixel 54 in which charge storage of frame i+1 finally starts among the pixels 54 of the simultaneous exposure lines. Alternatively, the timing of the global reset process is later than the timing at which the available storage period is started in the pixel 54 in which charge storage of frame i+1 finally starts among the pixels 54 of the simultaneous exposure lines. Among the pixels 54 of the simultaneous exposure lines, the pixel 54 in which the charge storage of frame i+1 finally starts is the pixel 54 of the eighth row.

The light source control unit 33 causes the light source 32 to be turned off at a timing at which the available storage period ends in the pixels 54 in which the charge storage of frame i+1 initially starts among the pixels 54 of the simultaneous exposure lines. The light source control unit 33 causes the light source 32 to be turned on after a timing at which the available storage period is started in the pixel 54 in which the charge storage of frame i+1 finally starts among the pixels 54 of the simultaneous exposure lines and before a timing at which the available storage period is started in the pixel 54 in which the charge storage of frame i+3 initially starts among the pixels 54 of the simultaneous exposure lines. Among the pixels 54 of the simultaneous exposure lines, the pixel 54 in which the charge storage of frame i+3 initially starts is the pixel 54 of the second row.

As described above, during a period in which the available storage periods of the pixels 54 in all the simultaneous exposure lines overlap, the imaging device control unit 30 causes the imaging device 21 to perform a scan for reading pixel signals from the pixels 54 in the non-simultaneous exposure lines. Thereby, the pixel signals constituting the image of frame i+1 are read from the pixels 54 in the non-simultaneous exposure lines. During a period from time t31 to time t32 shown in FIG. 23, the pixel signals of the pixels 54 in the odd-numbered rows which are non-simultaneous exposure lines are read. Thereafter, during a period from time t32 to time t34, the pixel signals constituting the image of frame i+1 are read from the pixels 54 in all the simultaneous exposure lines by the first scan. The imaging device 21 generates an image (a first image) using the pixel signals read by the first scan during the period from time t32 to time t34.

At time t32 shown in FIG. 23, reading of pixel signals of the pixels 54 of the second row is started. Thereafter, at time t34, reading of pixel signals of the pixels 54 of the eighth row is completed. During a period from time t32 to time t34, pixel signals of pixels 54 of the simultaneous exposure lines are read. The light source 32 is turned off during this period. In other words, in FIG. 23, the light source 32 is turned off during a period in which the pixel signals of the pixels 54 of the simultaneous exposure lines are read. The light source control unit 33 causes the light source 32 to be turned off at a timing at which reading of the pixel signals of frame i+1 is started in the pixels 54 from which the pixel signals are first read among the pixels 54 of the simultaneous exposure lines. Alternatively, after the timing of the global reset process and before the timing at which the reading of the pixel signals of frame i+1 is started in the pixels 54 from which the pixel signals are first read among the pixels 54 of the simultaneous exposure lines, the light source control unit 33 causes the light source 32 to be turned off. The light source control unit 33 causes the light source 32 to be maintained in a turned-off state during a period including a period during which the pixel signals of the pixels 54 of the simultaneous exposure lines are read.

An image of frame i+1 is used by the rolling distortion determination unit 342. The exposure time of the pixels 54 of each non-simultaneous exposure line in frame i+1 differs according to each non-simultaneous exposure line. Thus, the display processing unit 341 controls the image processing unit 31 so that a video signal constituting the image of frame i+1 is not output to the display unit 5. The display unit 5 does not display the image of frame i+1. Therefore, the display unit 5 displays only the image of frame i between the image of frame i+1 (the first image) and the image of frame i (the second image).

As described above, when the global exposure mode is set, the imaging device control unit 30 causes the imaging device 21 to perform the second scan during a period shorter than the frame cycle. The imaging device 21 generates a third image using pixel signals read by the second scan in the global exposure mode. The display unit 5 may display only the image of frame i and the third image among the image of frame i+1 (the first image), the image of frame i (the second image), and the third image.

At time t34, reading of the pixel signals of frame i+2 of the pixels 54 of the first row is started. At time t34, the light source control unit 33 switches the light source 32 from the turned-off state to the turned-on state. Thereafter, pixel signals of the pixels 54 of each row are read by the second scan. The pixel signals read from all the pixels 54 by this second scan constitute the image of frame i+2. The exposure time of the pixels 54 of each row in frame i+2 differs according to each row. Thus, the display processing unit 341 controls the image processing unit 31 so that a video signal constituting the image of frame i+2 is not output to the display unit 5. The display unit 5 does not display the image of frame i+2.

In frame i+1, during a period (a period from time t31 to time t32) other than a period during which the pixel signals of frame i+1 are read from the pixels 54 in all the simultaneous exposure lines by the first scan, all the pixels 54 in the simultaneous exposure lines can be exposed at the same time. During a period in which all the pixels 54 in the simultaneous exposure lines are simultaneously exposed, the pixel signals of frame i+1 are read from the pixels 54 in all non-simultaneous exposure lines.

In FIG. 23, because the simultaneous exposure lines or the non-simultaneous exposure lines are four rows, i.e., because the number of simultaneous exposure lines or the number of non-simultaneous exposure lines is half of the total number of rows of the pixels 54 of the imaging device 21, the exposure time of the pixels 54 in the simultaneous exposure lines is half of the frame cycle. If the simultaneous exposure lines are more than 4 rows, the non-simultaneous exposure lines are less than four rows. In this case, the exposure time of the pixels 54 in the simultaneous exposure lines is shorter than half of the frame cycle. If the simultaneous exposure lines are less than 4 rows, the non-simultaneous exposure lines are more than four rows. In this case, the exposure time of the pixels 54 in the simultaneous exposure lines can be made longer than half of the frame cycle. When the SG exposure mode is set, the light source control unit 33 controls the turning-on time of the light source 32 in accordance with the number of simultaneous exposure lines.

In the operation of each frame shown in FIG. 23, a time required for reading the pixel signals of all the pixels 54 is the same as the frame cycle. Thus, high-speed reading driving is unnecessary.

As shown in FIG. 23, the simultaneous exposure line is an even-numbered row, but the simultaneous exposure line may be an odd-numbered row. Groups of simultaneous exposure lines may be formed of n consecutive rows and n rows which are non-simultaneous exposure lines may be disposed between the two groups. n is an integer of 2 or more. For example, when n is 2, the simultaneous exposure lines are first and second rows, fifth and sixth rows, ninth and tenth rows, and the like.

Figure 24:
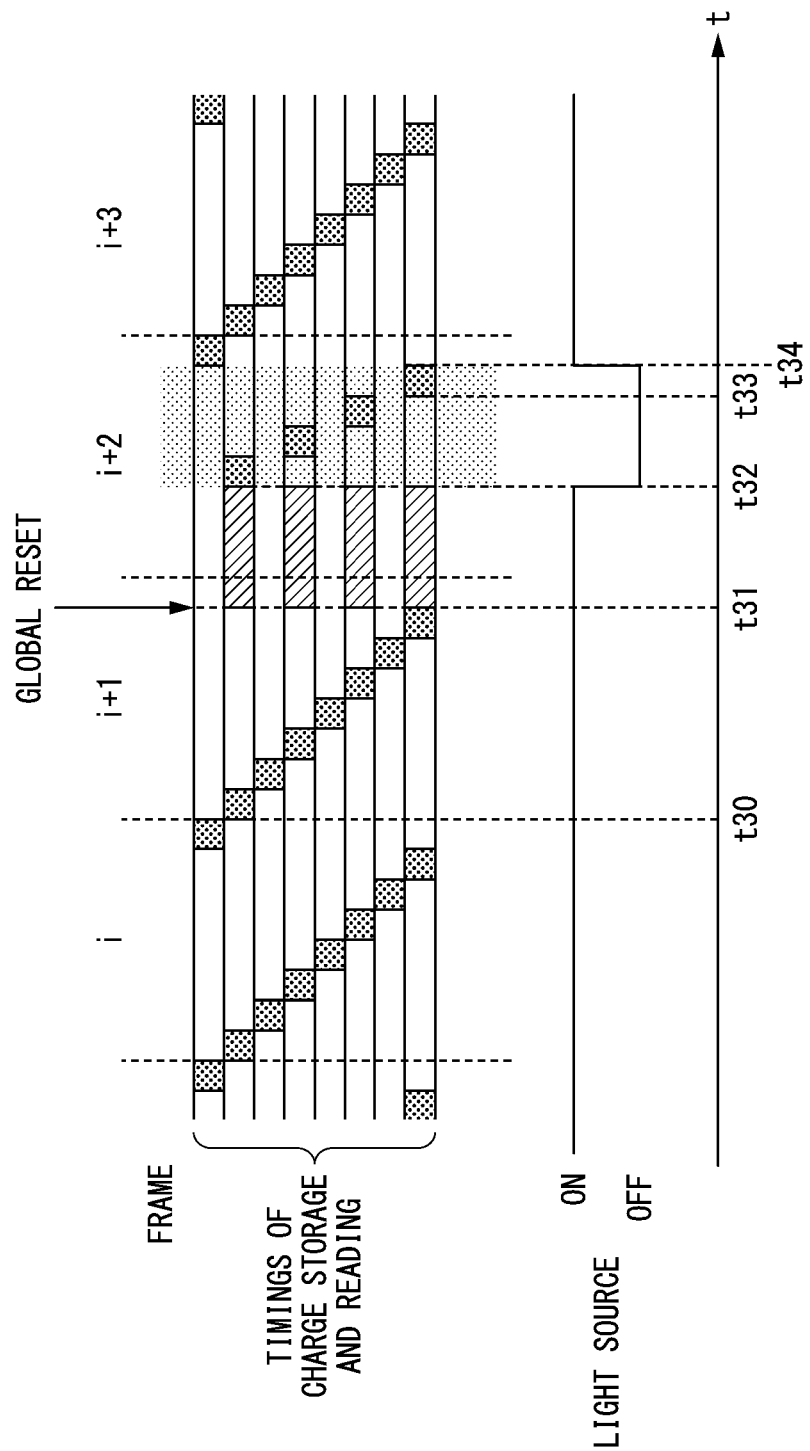
FIG. 24 is a timing chart showing the operations of the imaging device and the light source in the fifth embodiment of the present invention.

The operation shown in FIG. 23 may be changed to the operation shown in FIG. 24. In FIG. 24, reading of pixel signals constituting the image of frame i+1 is thinned reading. In other words, the pixel signals of the pixels 54 of the non-simultaneous exposure lines are not read during a period from time t31 to time t32. When the SG exposure mode is set, the imaging device control unit 30 causes the imaging device 21 to perform a first scan for reading pixel signals from the pixels 54 in the simultaneous exposure lines by consecutively scanning only all the simultaneous exposure lines. In this case, all the pixel signals read from the pixels 54 constitute the reference image of frame i+1. Thus, it is possible to omit a process in a subsequent stage of the imaging device 21. In order to make a data size of frame i+1 the same as data sizes of previous and subsequent frames, dummy data (for example, 0) may be added to the pixel signals of frame i+1 to form the reference image.

In the operation shown in FIG. 8 in the first embodiment, reading of pixel signals constituting images of frame i+1 and frame i+2 may be changed to thinning reading. In other words, during a period from time t24 to time t27 and a period from time t27 to time t29, only the pixel signals of the pixels 54 of the simultaneous exposure lines may be read and the pixel signals of the pixels 54 of the non-simultaneous exposure lines may not be read.

The CPU 34 in the endoscope apparatus 1 of the fifth embodiment may be changed to a CPU 34a shown in FIG. 15.

In the fifth embodiment, the start timings of the available charge storage periods of the pixels 54 in the simultaneous exposure lines are the same in the global reset process. Thus, it is unnecessary to turn off the light source 32 before the simultaneous exposures of the pixels 54 in the simultaneous exposure lines are started. In the first embodiment, the exposure is bad in frame i+1 before frame i+2 for which the simultaneous exposures of the pixels 54 in the simultaneous exposure lines are performed and the exposure is bad in frame i+3 subsequent to frame i+2. However, in the fifth embodiment, the exposure is bad in only frame i+2 after frame i+1 for which simultaneous exposures of the pixels 54 in the simultaneous exposure lines are performed. Thus, in the fifth embodiment, the operation in frame i+3 can be the same as the operation in frame i. As a result, it is possible to speed up the operation until the image recording process or the measurement process is executed from the input of the image recording instruction or the measurement instruction to the endoscope apparatus 1.

Sixth Embodiment

A sixth embodiment of the present invention will be described using the endoscope apparatus 1 shown in FIGS. 1 and 2. In an interline exposure mode in the sixth embodiment, after pixel signals are read from the pixels 54 of odd-numbered rows and pixel signals are read from the pixels 54 of even-numbered rows. In the global exposure mode in the sixth embodiment, as in the first embodiment, pixel signals are read from the pixels 54 in an arrangement order of rows.

Figure 25:
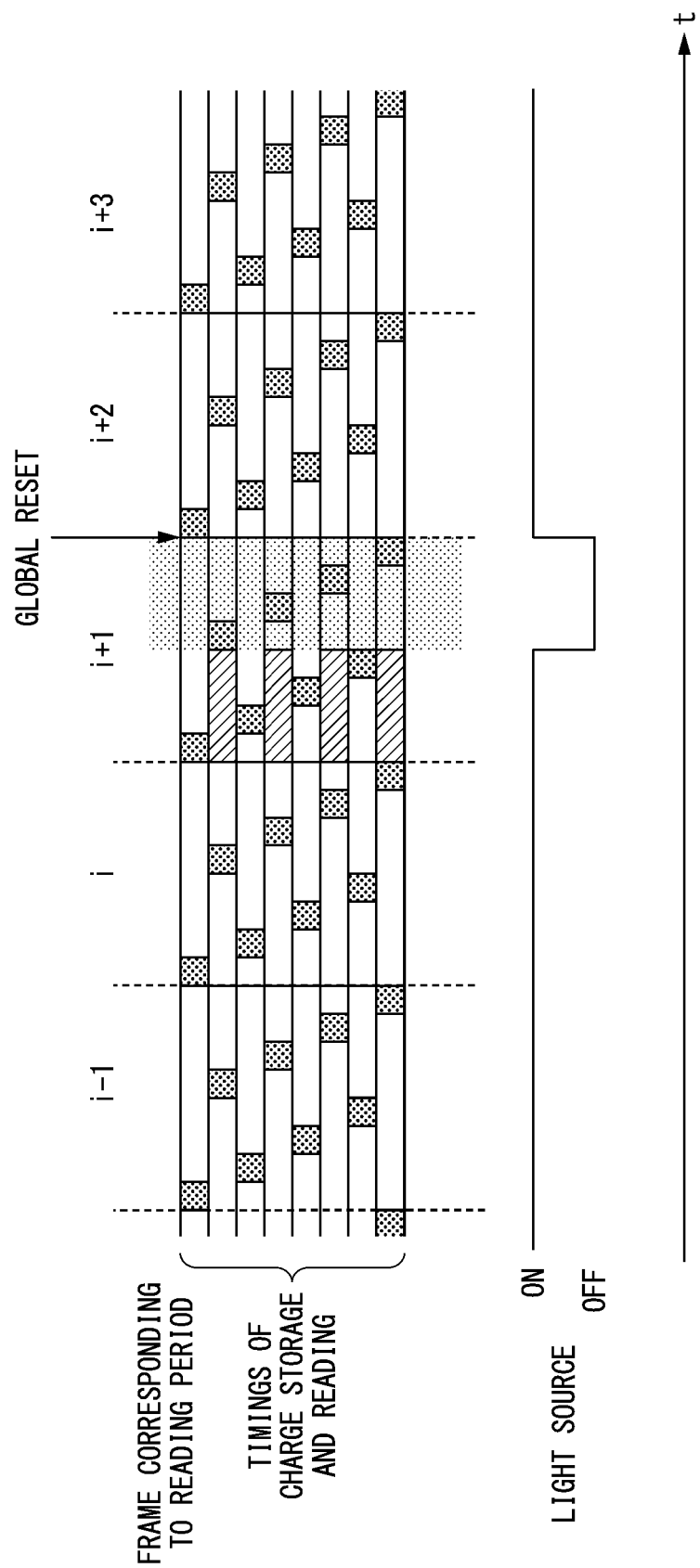
FIG. 25 is a timing chart showing operations of an imaging device and a light source in a sixth embodiment of the present invention.

FIG. 25 shows operations of an imaging device 21 and a light source 32 in a mode in which interline exposure and SG exposure are combined. In the upper-side drawing of FIG. 25, a horizontal direction indicates time and a vertical direction indicates a position of a row of the pixels 54 of the imaging device 21. In FIG. 25, the operations in the pixels 54 of eight rows are shown. A top row is a first row and a bottom row is an eighth row. In the lower-side drawing of FIG. 25, a lateral direction indicates time and a longitudinal direction indicates a state of the light source 32. "ON" indicates a state in which the light source 32 is turned on. "OFF" indicates a state in which the light source 32 is turned off.

In FIG. 25, timings of charge storage and reading of each row in an array of a plurality of pixels 54 is shown. In FIG. 25, unlike the timing chart of FIG. 24 and the like, a frame cycle based on the start timing of reading of pixel signals in the pixels 54 in the first row is shown. In frame i−1 and frame i, an operation based on an interline exposure mode as a second mode is performed. When the interline exposure mode is set, the imaging device 21 consecutively scans the odd-numbered rows and then consecutively scans the even-numbered rows. Thereby, the imaging device control unit 30 causes the imaging device 21 to perform the second scan for reading the pixel signals from the pixels 54 in all of the plurality of rows by consecutively scanning all of the plurality of rows.

In frame i+1, an operation based on an SG exposure mode that is a first mode is performed. Frame i+1 is a frame for performing the SG exposure. In FIG. 25, the simultaneous exposure line is an even-numbered row. The operation of reading the pixel signal of each pixel 54 in the SG exposure mode is the same as the operation of reading the pixel signal of each pixel 54 in the interline exposure mode. In frame i+2 and frame i+3, the operation based on the interline exposure mode that is the second mode is performed. The operation of reading the pixel signals of the pixels 54 of frame i+2 and frame i+3 is the same as the operation of reading pixel signals of the pixels 54 of frame i−1 and frame i.

In the sixth embodiment, when the SG exposure mode is set, the imaging device control unit 30 causes the imaging device 21 to consecutively perform a first scan for reading pixel signals from the pixels 54 in simultaneous exposure lines by consecutively scanning all the simultaneous exposure lines and consecutively perform a third scan for reading pixel signals from the pixels 54 in non-simultaneous exposure lines by consecutively scanning all the non-simultaneous exposure lines other than the simultaneous exposure lines among a plurality of rows in an array of the plurality of pixels 54. In the sixth embodiment, when the interline exposure mode is set, the imaging device control unit 30 causes the imaging device 21 to perform a second scan for reading the pixel signals from the pixels 54 in all of the plurality of rows by consecutively scanning all of the plurality of rows in the array of the plurality of pixels 54. The second scan in the sixth embodiment includes the first scan and the third scan. An order in which rows are scanned by the second scan is the same as an order in which rows are scanned by consecutively performing the first and third scans.

The operation of the imaging device 21 in the sixth embodiment may be applied to the second embodiment. A blur determination unit 346 may determine a situation of occurrence of a motion blur in a second image by comparing the image of the odd-numbered row and the image of the even-numbered row acquired in the interline exposure mode. The determination of the situation of occurrence of the motion blur may be performed by a blur calculation process disclosed in Japanese Unexamined Patent Application, First Publication No. 2014-210194. An image of odd-numbered rows in the sixth embodiment corresponds to an odd-numbered field image in Japanese Unexamined Patent Application, First Publication No. 2014-210194 and an image of even-numbered rows in the sixth embodiment corresponds to an even-numbered field image in Japanese Unexamined Patent Application, First Publication No. 2014-210194. In this case, the blur determination unit 346 uses an image of only one frame to determine a situation of occurrence of a motion blur. Thus, it is possible to reduce the number of images necessary for determining the situation of occurrence of the motion blur of the second image. As a result, after the image recording instruction or the measurement instruction is input to the endoscope apparatus 1, it is possible to speed up the operation until the image recording process or the measurement process is executed.

In the interline exposure mode and the SG exposure mode of the sixth embodiment, control for switching an order in which pixel signal reading is performed is unnecessary. Thus, heat generation of the imaging device 21 can be further suppressed. In the sixth embodiment, a similar effect can be obtained even if the simultaneous exposure lines are odd-numbered rows.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope apparatus comprising:
a light source configured to generate illumination light for illuminating a subject;
an optical system configured to form an optical image of the subject illuminated with the illumination light;
an imaging device comprising a plurality of pixels disposed in a matrix and configured to generate pixel signals of the pixels based on the optical image in each of a plurality of frames and generate an image of the subject using the pixel signals; and
a processor configured to:
switch between settings of a first mode and a second mode;
in response to the first mode being set,
cause the imaging device to perform a first scan for reading the pixel signals from the pixels in simultaneous exposure lines by consecutively scanning all the simultaneous exposure lines, the simultaneous exposure lines being some of a plurality of rows in an array of the plurality of pixels;
cause the light source to be turned on during a first period and cause the light source to be turned off during a period including all of a second period,
wherein the first period is a period including all or a part of a period during which available storage periods of the pixels in all the simultaneous exposure lines overlap, and
wherein the second period is a period during which a scan is performed for reading the pixel signals generated by the pixels in all the simultaneous exposure lines from the pixels during the first period; and
cause the imaging device to generate a first image using the pixel signals generated by the pixels in all the simultaneous exposure lines during the period in which the available storage periods of the pixels in all the simultaneous exposure lines overlap;
in response to the second mode being set, the processor is configured to:
cause the imaging device to perform a second scan for reading the pixel signals from the pixels in the plurality of rows by consecutively scanning the plurality of rows;
cause the light source to be turned on during a period including all of the available storage periods of the pixels in each of the plurality of rows before the second scan is performed; and
cause the imaging device to generate a second image using the pixel signals read by the second scan; and
determine a situation of an occurrence of a rolling distortion using the first image and the second image.

2. The endoscope apparatus according to claim 1, wherein the processor is configured to determine the situation of the occurrence of the rolling distortion using data of the simultaneous exposure lines of the first image and data of rows corresponding to the simultaneous exposure lines of the first image in the second image.

3. The endoscope apparatus according to claim 1,
wherein the processor is configured to cause the imaging device to read the pixel signals of a second frame from the pixels in rows including all the simultaneous exposure lines after the pixel signals of a first frame are read from the pixels in all the simultaneous exposure lines by the first scan,
wherein the imaging device is configured to generate the first image using the pixel signals of the second frame,
wherein after a scan of all the simultaneous exposure lines by the first scan is completed, the processor is configured to cause the light source to be turned on during a period including all or a part of a period during which the available storage periods of the pixels in all the simultaneous exposure lines overlap and causes the light source to be turned off during a period including all of a period during which the first scan is performed, and
wherein the processor is configured to cause the light source to be turned off during a period in which the pixel signals of the second frame are read from the pixels in the simultaneous exposure lines.

4. The endoscope apparatus according to claim 1,
wherein, in response to the first mode being set, the processor is configured to cause the imaging device to simultaneously reset the pixels in all the simultaneous exposure lines,
wherein after the pixels in all the simultaneous exposure lines are simultaneously reset, the processor is configured to cause the imaging device to perform the first scan,
wherein the imaging device is configured to generate the first image using the pixel signals read by the first scan, and
wherein after the pixels in all the simultaneous exposure lines are simultaneously reset, the processor is configured to cause the light source to be turned on during the first period and cause the light source to be turned off during a period including all of a period during which the first scan is performed.

5. The endoscope apparatus according to claim 1,
wherein the processor is configured to determine a situation of occurrence of a blur in the first image,
wherein, in response to an instruction of any one of freezing, image recording, and measurement being accepted, the processor is configured to set the first mode, and
wherein, in response to determining that a blur in the first image is less than or equal to a predetermined amount, the processor is configured to set the second mode.

6. The endoscope apparatus according to claim 1,
wherein the processor is configured to determine a situation of occurrence of a blur in the first image and the second image,
wherein, in response to an instruction of any one of freezing, image recording, and measurement being accepted, the processor is configured to determine a situation of occurrence of a blur in the second image,
wherein in response to determining that a blur in the second image is less than or equal to a predetermined amount, the processor is configured to set the first mode, and
wherein in response to determining that a blur in the first image is less than or equal to a predetermined amount, the processor is configured to set the second mode.

7. The endoscope apparatus according to claim 1, wherein the processor is configured to perform a process using the second image for which the rolling distortion is determined to be less than or equal to a predetermined amount.

8. The endoscope apparatus according to claim 7, wherein the processor is configured to cause the second image for which the rolling distortion is determined to be less than or equal to the predetermined amount to be stored in a memory after an image recording instruction is accepted.

9. The endoscope apparatus according to claim 7, wherein the processor is configured to perform measurement of the subject using the second image for which the rolling distortion is determined to be less than or equal to the predetermined amount after a measurement instruction is accepted.

10. The endoscope apparatus according to claim 1, further comprising a temperature sensor configured to measure a temperature of the imaging device,
wherein the processor is configured to:
perform switching between the first mode, the second mode, and a third mode;
in response to the temperature being greater than a predetermined value, sequentially set the first mode and the second mode;
in response to the temperature being less than or equal to the predetermined value, set the third mode;
in response to the third mode being set, cause the imaging device to perform the second scan during a period shorter than a frame cycle;
cause the imaging device to generate a third image using the pixel signals read by the second scan in the third mode;
cause the light source to be turned on during a period including all or a part of a period during which the available storage periods of the pixels in each of the plurality of rows overlap before the second scan is performed in the third mode; and
cause the light source to be turned off during a period in which the second scan is performed in the third mode.

11. The endoscope apparatus according to claim 10, wherein the processor is configured to cause a display to display only the second image among the first image, the second image, and the third image.

12. The endoscope apparatus according to claim 10, wherein the processor is configured to cause a display to display only the second image and the third image among the first image, the second image, and the third image.

13. The endoscope apparatus according to claim 1, wherein the processor is configured to cause a display to display only the second image.

14. The endoscope apparatus according to claim 13, wherein the processor is configured to cause the display to display a warning in response to determining that the rolling distortion greater than a predetermined amount has occurred.

15. The endoscope apparatus according to claim 14, wherein the processor is configured to perform a process using the second image for which the rolling distortion is determined to be less than or equal to the predetermined amount when a processing instruction is accepted after the display displays the warning.

16. The endoscope apparatus according to claim 13, wherein, after a freeze instruction is accepted, the processor is configured to cause the display to perform a freeze image displaying process on the second image for which the rolling distortion is determined to be less than or equal to a predetermined amount.

17. The endoscope apparatus according to claim 1, wherein the processor is configured to cause a display to display the situation of the occurrence of the rolling distortion determined.

18. A method for controlling an endoscope apparatus, the endoscope apparatus comprising:
a light source configured to generate illumination light for illuminating a subject;
an optical system configured to form an optical image of the subject illuminated with the illumination light; and
an imaging device comprising a plurality of pixels disposed in a matrix and configured to generate pixel signals of the pixels based on the optical image in each of a plurality of frames and generate an image of the subject using the pixel signals,
wherein the method comprises:
switching between settings of a first mode and a second mode;
in response to the first mode being set,
causing the imaging device to perform a first scan for reading the pixel signals from the pixels in simultaneous exposure lines by consecutively scanning all the simultaneous exposure lines, the simultaneous exposure lines being some of a plurality of rows in an array of the plurality of pixels;

causing the light source to be turned on during a first period and causing the light source to be turned off during a period including all of a second period, wherein the first period is a period including all or a part of a period during which available storage periods of the pixels in all the simultaneous exposure lines overlap, and wherein the second period is a period during which a scan is performed for reading the pixel signals generated by the pixels in all the simultaneous exposure lines from the pixels during the first period; and causing the imaging device to generate a first image using the pixel signals generated by the pixels in all the simultaneous exposure lines during the period in which the available storage periods of the pixels in all the simultaneous exposure lines overlap;

in response to the second mode being set, the processor is configured to:

causing the imaging device to perform a second scan for reading the pixel signals from the pixels in the plurality of rows by consecutively scanning the plurality of rows;

causing the light source to be turned on during a period including all of the available storage periods of the pixels in each of the plurality of rows before the second scan is performed; and causing the imaging device to generate a second image using the pixel signals read by the second scan; and determining a situation of an occurrence of a rolling distortion using the first image and the second image.

19. A non-transitory computer-readable storage medium storing instructions for controlling an endoscope apparatus, the endoscope apparatus comprising:

a light source configured to generate illumination light for illuminating a subject;

an optical system configured to form an optical image of the subject illuminated with the illumination light; and an imaging device comprising a plurality of pixels disposed in a matrix and configured to generate pixel signals of the pixels based on the optical image in each of a plurality of frames and generate an image of the subject using the pixel signals, wherein the instructions cause a computer to at least perform:

switching between settings of a first mode and a second mode;

in response to the first mode being set, causing the imaging device to perform a first scan for reading the pixel signals from the pixels in simultaneous exposure lines by consecutively scanning all the simultaneous exposure lines, the simultaneous exposure lines being some of a plurality of rows in an array of the plurality of pixels;

causing the light source to be turned on during a first period and causing the light source to be turned off during a period including all of a second period, wherein the first period is a period including all or a part of a period during which available storage periods of the pixels in all the simultaneous exposure lines overlap, and wherein the second period is a period during which a scan is performed for reading the pixel signals generated by the pixels in all the simultaneous exposure lines from the pixels during the first period; and causing the imaging device to generate a first image using the pixel signals generated by the pixels in all the simultaneous exposure lines during the period in which the available storage periods of the pixels in all the simultaneous exposure lines overlap;

in response to the second mode being set, the processor is configured to:

causing the imaging device to perform a second scan for reading the pixel signals from the pixels in the plurality of rows by consecutively scanning the plurality of rows;

causing the light source to be turned on during a period including all of the available storage periods of the pixels in each of the plurality of rows before the second scan is performed; and causing the imaging device to generate a second image using the pixel signals read by the second scan; and determining a situation of an occurrence of a rolling distortion using the first image and the second image.

* * * * *